US011529377B2

(12) United States Patent
Kim

(10) Patent No.: US 11,529,377 B2
(45) Date of Patent: Dec. 20, 2022

(54) **NANO-VESICLES DERIVED FROM GENUS *SPHINGOMONAS* BACTERIA AND USE THEREOF**

(71) Applicant: MD HEALTHCARE INC., Seoul (KR)

(72) Inventor: Yoon-Keun Kim, Gyeonggi-do (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 16/631,491

(22) PCT Filed: Nov. 20, 2019

(86) PCT No.: PCT/KR2019/015902
§ 371 (c)(1),
(2) Date: Jan. 16, 2020

(87) PCT Pub. No.: WO2020/122450
PCT Pub. Date: Jun. 18, 2020

(65) Prior Publication Data

US 2022/0062353 A1 Mar. 3, 2022

(30) Foreign Application Priority Data

Dec. 10, 2018 (KR) ........................ 10-2018-0158623
Oct. 23, 2019 (KR) ........................ 10-2019-0132138

(51) Int. Cl.

| | |
|---|---|
| ***A61K 35/74*** | (2015.01) |
| ***A23L 33/135*** | (2016.01) |
| ***A61P 29/00*** | (2006.01) |
| ***A61K 8/99*** | (2017.01) |
| ***C12Q 1/6806*** | (2018.01) |
| ***C12Q 1/689*** | (2018.01) |

(52) U.S. Cl.
CPC ............ *A61K 35/74* (2013.01); *A23L 33/135* (2016.08); *A61K 8/99* (2013.01); *A61P 29/00* (2018.01); *C12Q 1/6806* (2013.01); *C12Q 1/689* (2013.01)

(58) Field of Classification Search
CPC .......... A61Q 19/00; A61P 17/00; A61P 29/00; A61K 35/74
See application file for complete search history.

(56) References Cited

FOREIGN PATENT DOCUMENTS

| | | | | |
|---|---|---|---|---|
| EP | 0887070 | A1 | 12/1998 | |
| EP | 3483284 | | 5/2019 | |
| EP | 3567118 | | 11/2019 | |
| EP | 3696284 | | 8/2020 | |
| KR | 20110025068 | A | 3/2011 | |
| KR | 20160032722 | | 3/2016 | |
| KR | 101745809 | | 6/2017 | |
| KR | 20180006303 | A | 1/2018 | |
| KR | 20180098149 | | 9/2018 | |
| KR | 20180129627 | | 12/2018 | |
| RU | 2727540 | | 7/2020 | |
| WO | 2014039503 | A1 | 3/2014 | |
| WO | 2016144139 | A2 * | 9/2016 | ........... A61K 35/747 |
| WO | 2018111028 | A1 | 6/2018 | |
| WO | 2018216912 | A1 | 11/2018 | |
| WO | 2018216912 | A1 | 11/2018 | |
| WO | 2019074216 | A1 | 4/2019 | |

OTHER PUBLICATIONS

Bryan, PF et al., "Sphingolipids as Mediators in the Crosstalk between Microbiota and Intestinal Cells: Implications for Inflammatory Bowel Disease", Mediators of Inflammation, vol. 2016, pp. 1-11. (Year: 2016).*
Lee, JS et al., "*Sphingomonas aquatilis* sp. nov., *Sphingomonas koreensis* sp. nov. and *Sphingomonas taejonensis* sp. nov., yellow-pigmented bacteria isolated from natural mineral water", International Journal of Systematic and Evolutionary Microbiology, vol. 51, pp. 1491-1498. (Year: 2001).*
Kim, JH et al., "Gram-negative and Gramp-positive bacterial extracellular veiscles", Seminars in Cell & Developmental Biology, vol. 40, pp. 97-104. (Year: 2015).*
International Search Report for App. No. PCT/KR2019/015902, dated Feb. 25, 2020, 7 pages.
Russian Office Action for App. No. 2021104795, dated Dec. 12, 2021.
Gyorgy B et al. 2015, "Therapeutic applications of extracellular vesicles: clinical promise and open questions", Annual review of pharmacology and toxicology, 55:439-464.
Khan M. A. et al. 2018 "Liposomal formulation of glycosphingolipids from Sphingomonas paucimobilis induces antitumour immunity in mice", Journal of drug targeting, 26:709-719.
Translation of Office Action No. 1 for Japanese Patent Application 2021-510417, drafted Feb. 14, 2022.
Jiang, "Japanese Journal of Lactic Acid Bacteria", 2012, vol. 23, No. 1, p. 24-34—Considered english abstract.
Japanese First Office Action (including English translation) issued in JP2021-510417, dated Feb. 22, 2022, 15 pages.
Korenori, et al., "Current status and problems of 16S rRNA pyrosequencing-based profiling of gastro-intestinal icrobiota," Japanese Journal of Lactic Acid Bacteria, vol. 23, No. 1, 2012, pp. 24-34 (English abstract attached).—Considered english abstract.

(Continued)

*Primary Examiner* — Michelle F. Paguio Frising
*Assistant Examiner* — Grant C Currens
(74) *Attorney, Agent, or Firm* — Riverside Law LLP

(57) ABSTRACT

The present invention relates to vesicles derived from bacteria belonging to the genus *Sphingomonas* and compositions as well as uses thereof. In some embodiments, the composition is a drug carrier which delivers a drug to the brain. In some embodiments, the invention provides a method of suppressing the secretion inflammatory mediators by pathogenic vesicles using said vesicles derived from bacteria belonging to the genus *Sphingomonas* or compositions thereof. In some embodiments, the invention provides methods of diagnosing hepatic cirrhosis, liver cancer, myocardial infarction, renal insufficiency, diabetes, brain tumors, mild cognitive impairment, dementia, depression, autism, and/or atopic dermatitis.

4 Claims, 21 Drawing Sheets

Specification includes a Sequence Listing.

(56) References Cited

OTHER PUBLICATIONS

Translation of Office Action No. 1 for Japanese Patent Application 2021-510417, drafted Feb. 14, 2022.—pp. 1-15.
Agarwal, Srishti et al., "Vesicular systems employing natural substances as promising drug candidates for MMP nhibition in glioblastoma: A nanotechnological approach", International Journal of Pharmaceutics, Elsevier, NL, vol. 551, No. 1, Sep. 17, 2018, pp. 339-361, XP085495904.
Extended European Search Report issued in App. No. EP19896521.2, dated Jul. 18, 2022, 11 pages.
Yang, Jinho et al: "Microbe-derived extracellular vesicles as a smart drug delivery system", Translational and Clinical Pharmacology, vol. 26, No. 3, Jan. 1, 2018 (Jan. 1, 2018), p. 103, XP055940292, ISSN 2289-0882, DOI: 10.12793/tcp.2018.26.3.103.

* cited by examiner

SPC101: *Sphingomonas paucimobilis* EV

SPC101 : *Sphingomonas paucimobilis* EV

SPC102: *Sphingomonas koreensis* EV

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
```

-continued

```
<220> FEATURE:
<223> OTHER INFORMATION: 16S_V3_F
<220> FEATURE:
<221> NAME/KEY: misc_feature
<222> LOCATION: (42)..(42)
<223> OTHER INFORMATION: any nucleotide

<400> SEQUENCE: 1

tcgtcggcag cgtcagatgt gtataagaga cagcctacgg gnggcwgcag            50


<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2

gtctcgtggg ctcggagatg tgtataagag acaggactac hvgggtatct aatcc       55
```

NANO-VESICLES DERIVED FROM GENUS *SPHINGOMONAS* BACTERIA AND USE THEREOF

CROSS-REFERENCE TO RELATED APPLICATIONS

This application is the U.S. national phase application filed under 35 U.S.C. § 371 claiming benefit to International Patent Application No. PCT/KR2019/015902, filed on Nov. 20, 2019, which claims priority to Korean Patent Application No. 10-2018-0158623, filed Dec. 10, 2018, and Korean Patent Application No. 10-2019-0132138, filed Oct. 23, 2019, the disclosures of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132_0083_00US_Sequence_Listing_ST25.txt" in ASCII format. The text file containing the Sequence Listing of the present application was created on Oct. 15, 2021 and is 791 bytes in size.

TECHNICAL FIELD

The present invention relates to nanovesicles derived from bacteria belonging to the genus *Sphingomonas* and a use thereof, and more particularly to a method for diagnosing hepatic cirrhosis, liver cancer, myocardial infarction, renal insufficiency, diabetes, brain tumors, mild cognitive impairment, dementia, depression, autism, and atopic dermatitis, and the like using nanovesicles derived from bacteria belonging to the genus *Sphingomonas*, a composition for preventing, alleviating, or treating the disease, comprising the vesicles, a composition for delivering a drug for treating a brain disease, comprising the vesicles, and the like.

This application claims priority to and the benefit of Korean Patent Application Nos. 10-2018-0158623 and 10-2019-0132138 filed in the Korean Intellectual Property Office on Dec. 10, 2018 and Oct. 23, 2019, respectively, and all the contents disclosed in the specifications and drawings of those applications are incorporated in this application.

BACKGROUND ART

Since the beginning of the 21st century, acute infectious diseases recognized as epidemic diseases in the past have become less important, whereas chronic diseases accompanied by immune dysfunction caused by disharmony between humans and microbiomes have changed disease patterns as main diseases that determine the quality of life and the human lifespan. As an intractable chronic disease in the 21st century, cancer, cardiovascular diseases, allergic-chronic lung diseases, metabolic diseases, and neuropsychiatric diseases have become a big problem for public health in the country as main diseases that determine the human lifespan and the quality of life.

It is known that the number of microorganisms coexisting in the human body has reached 100 trillion, which is 10 times more than the number of human cells, and the number of microorganism genes is more than 100 times the number of human genes. A microbiota or microbiome refers to a microbial community including bacteria, archaea and eukarya present in a given habitat.

Bacteria coexisting in our body and bacteria present in the ambient environment secrete nanometer-sized vesicles in order to exchange information on genes, low molecular compounds, proteins, and the like with other cells. The mucosa forms a physical defense membrane through which particles having a size of 200 nanometers (nm) or more cannot pass, so that bacteria coexisting in the mucosa cannot pass through the mucosa, but vesicles derived from bacteria have a size of 100 nanometers or less and are absorbed into our bodies after relatively freely passing through epithelial cells via the mucosa. Bacteria-derived vesicles that are locally secreted from bacteria are absorbed via epithelial cells of the mucous membrane to thereby induce a local inflammatory response, and the vesicles having passed through the epithelial cells are systematically absorbed via lymphatic vessels and thereby distributed in respective organs, and immune and inflammatory responses are regulated in the organs in which the vesicles are distributed. For example, vesicles derived from pathogenic Gram-negative bacteria such as *Escherichia coli* locally induce inflammatory response and cancer, and promote systemic inflammatory responses and blood coagulation through vascular endothelial cell inflammatory responses when absorbed via the blood vessels. In addition, such vesicles are absorbed into muscle cells on which insulin acts, and the like to cause insulin resistance and diabetes. In contrast, vesicles derived from beneficial bacteria may regulate diseases by regulating immune functions and metabolic dysfunctions by pathogenic vesicles.

As immune responses to factors such as bacteria-derived vesicles, Th17 immune responses characterized by the secretion of the interleukin (hereinafter, IL)-17 cytokine occur, and IL-6 is secreted from epithelial cells and immune cells when exposed to bacteria-derived vesicles, thereby inducing Th17 immune responses. Inflammation caused by the Th17 immune response is characterized by neutrophil infiltration, and during the process by which inflammation occurs, tumor necrosis factor-alpha (hereinafter, TNF-$\alpha$) secreted from inflammatory cells such as neutrophils and macrophages plays an important role in inflammation and oncogenesis.

Bacteria belonging to the genus *Sphingomonas* are aerobic Gram-negative bacteria that widely inhabit nature such as water, soil, and plant roots, and other Gram-negative bacteria have a lipopolysaccharide (LPS) in the outer cell membrane, whereas bacteria belonging to the genus *Sphingomonas* have a glycosphingolipid (GSL) in the cell outer membrane. Twenty species of the genus *Sphingomonas* are known, and among them, *Sphingomonas paucimobilis* has been reported to cause hospital acquired infections in humans. However, no case has yet been reported in which vesicles derived from bacteria belonging to the genus *Sphingomonas* including the aforementioned bacteria are applied to the diagnosis and treatment of an incurable disease such as cancer, a cardiovascular disease, and atopic dermatitis.

Thus, in the present invention, it was confirmed that a disease could be diagnosed by confirming that vesicles derived from bacteria belonging to the genus *Sphingomonas* were significantly decreased in clinical samples of patients with hepatic cirrhosis, liver cancer, myocardial infarction, renal insufficiency, diabetes, brain tumors, and atopic dermatitis compared to normal individuals. Further, as a result of isolating vesicles from *Sphingomonas paucimobilis* and *Sphingomonas koreensis* belonging to genus *Sphingomonas* bacteria and analyzing characteristics thereof, it was confirmed that the vesicles could be used as a composition for preventing or treating a disease such as hepatic cirrhosis, liver cancer, myocardial infarction, renal insufficiency, diabetes, brain tumors, mild cognitive impairment, dementia, depression, autism, and atopic dermatitis. Further, it was confirmed that when the vesicles were orally administered, a drug could be delivered to the brain.

DISCLOSURE

Technical Problem

To address the above-described problems, as a result of having conducted intensive research, the inventors of the present invention confirmed through metagenomic analysis that the content of vesicles derived from bacteria belonging to the genus *Sphingomonas* was significantly reduced in samples derived from patients with hepatic cirrhosis, liver cancer, myocardial infarction, renal insufficiency, diabetes, brain tumors, mild cognitive impairment, dementia, depression, autism, and atopic dermatitis, compared to normal individuals. It was also confirmed that, when isolating vesicles from *Sphingomonas paucimobilis* and *Sphingomonas koreensis*, which is a bacterium belonging to the genus *Sphingomonas* and treating macrophages therewith, the secretion of IL-6 and TNF-α by pathogenic vesicles was significantly inhibited, thus completing the present invention based on these findings.

Thus, an object of the present invention is to provide a method of diagnosing one or more diseases selected from the group consisting of hepatic cirrhosis, liver cancer, myocardial infarction, renal insufficiency, diabetes, brain tumors, mild cognitive impairment, dementia, depression, autism, and atopic dermatitis, or a method of providing information for diagnosis.

Further, another object of the present invention is to provide a composition for preventing, alleviating or treating one or more diseases selected from the group consisting of hepatic cirrhosis, liver cancer, myocardial infarction, renal insufficiency, diabetes, brain tumors, mild cognitive impairment, dementia, depression, autism, and atopic dermatitis, comprising bacteria belonging to the genus *Sphingomonas*-derived vesicles as an active ingredient.

In addition, still another object of the present invention is to provide a composition for delivering a drug for treating a brain disease, comprising vesicles derived from bacteria belonging to the genus *Sphingomonas* as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a method of providing information for diagnosing one or more diseases selected from the group consisting of hepatic cirrhosis, liver cancer, myocardial infarction, renal insufficiency, diabetes, brain tumors, mild cognitive impairment, dementia, depression, autism, and atopic dermatitis, the method comprising the following steps:

(a) extracting DNAs from vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) determining a case in which a content of vesicles derived from bacteria belonging to the genus *Sphingomonas* is lower than that of the normal individual sample, as one or more diseases selected from the group consisting of hepatic cirrhosis, liver cancer, myocardial infarction, renal insufficiency, diabetes, brain tumors, mild cognitive impairment, dementia, depression, autism, and atopic dermatitis, through quantitative analysis of the PCR product.

In addition, the present invention provides a method of diagnosing one or more diseases selected from the group consisting of hepatic cirrhosis, liver cancer, myocardial infarction, renal insufficiency, diabetes, brain tumors, mild cognitive impairment, dementia, depression, autism, and atopic dermatitis, the method comprising the following steps:

(a) extracting DNAs from vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) determining a case in which a content of vesicles derived from bacteria belonging to the genus *Sphingomonas* is lower than that of the normal individual sample, as one or more diseases selected from the group consisting of hepatic cirrhosis, liver cancer, myocardial infarction, renal insufficiency, diabetes, brain tumors, mild cognitive impairment, dementia, depression, autism, and atopic dermatitis, through quantitative analysis of the PCR product.

As an exemplary embodiment of the present invention, the sample in Step (a) may be blood or urine.

As another embodiment of the present invention, the primer pair in Step (b) may be a primer pair comprising base sequences represented by SEQ ID Nos. 1 and 2.

Further, the present invention provides a composition for preventing, alleviating, or treating one or more diseases selected from the group consisting of hepatic cirrhosis, liver cancer, myocardial infarction, renal insufficiency, diabetes, brain tumors, mild cognitive impairment, dementia, depression, autism, and atopic dermatitis, comprising vesicles derived from bacteria belonging to the genus *Sphingomonas* as an active ingredient.

The composition may comprise a pharmaceutical composition, a food composition, and a cosmetic composition.

Furthermore, the present invention provides a method of preventing or treating one or more diseases selected from the group consisting of hepatic cirrhosis, liver cancer, myocardial infarction, renal insufficiency, diabetes, brain tumors, mild cognitive impairment, dementia, depression, autism, and atopic dermatitis, the method comprising a step of administering a composition comprising vesicles derived from bacteria belonging to the genus *Sphingomonas* as an active ingredient to a subject.

Further, the present invention provides a use of vesicles derived from bacteria belonging to the genus *Sphingomonas* for preventing or treating one or more diseases selected from the group consisting of hepatic cirrhosis, liver cancer, myocardial infarction, renal insufficiency, diabetes, brain tumors, mild cognitive impairment, dementia, depression, autism, and atopic dermatitis.

Further, the present invention provides a use of a composition comprising vesicles derived from bacteria belonging to the genus *Sphingomonas* as an active ingredient for preventing or treating one or more diseases selected from the group consisting of hepatic cirrhosis, liver cancer, myocardial infarction, renal insufficiency, diabetes, brain tumors, mild cognitive impairment, dementia, depression, autism, and atopic dermatitis.

In addition, the present invention provides a use of vesicles derived from bacteria belonging to the genus *Sphingomonas* for producing a medicine used for one or more diseases selected from the group consisting of hepatic cirrhosis, liver cancer, myocardial infarction, renal insufficiency, diabetes, brain tumors, mild cognitive impairment, dementia, depression, autism, and atopic dermatitis.

Furthermore, the present invention provides a drug carrier composition which delivers a drug to the brain (or a composition for delivering a drug for treating a brain disease), comprising vesicles derived from bacteria belonging to the genus *Sphingomonas* as an active ingredient.

Further, the present invention provides a method of delivering a drug for treating a brain disease, the method comprising administering, to a subject, a composition comprising bacteria belonging to the genus *Sphingomonas*-derived vesicles in which a drug for treating a target brain disease is loaded as an active ingredient.

In addition, the present invention provides a use of vesicles derived from bacteria belonging to the genus *Sphingomonas* for delivering a drug for treating a brain disease.

As an exemplary embodiment of the present invention, the vesicles may have an average diameter of 10 to 200 nm.

As another exemplary embodiment of the present invention, the vesicles may be secreted naturally or artificially from bacteria belonging to the genus *Sphingomonas*.

As still another embodiment of the present invention, the vesicles may be secreted by performing a method such as heat treatment and pressure treatment on the bacteria.

As yet another embodiment of the present invention, the vesicles derived from bacteria belonging to the genus *Sphingomonas* may be secreted from *Sphingomonas paucimobilis*.

As yet another embodiment of the present invention, the vesicles derived from bacteria belonging to the genus *Sphingomonas* may be secreted from *Sphingomonas koreensis*.

Advantageous Effects

The present inventors confirmed that bacteria are not absorbed into the body, but vesicles derived from bacteria are absorbed into the body through epithelial cells, systemically distributed, and excreted from the body through the kidneys, liver, and lungs, and that through a metagenomic analysis of vesicles derived from bacteria present in the blood of a patient, vesicles derived from bacteria belonging to a genus *Sphingomonas* present in the blood or urine of patients with hepatic cirrhosis, liver cancer, myocardial infarction, renal insufficiency, diabetes, brain tumors, mild cognitive impairment, dementia, depression, autism, and atopic dermatitis had been significantly decreased as compared to those in normal individual. Further, it was observed that when genus *Sphingomonas* bacteria *Sphingomonas paucimobilis* and *Sphingomonas koreensis* were cultured ex vivo and vesicles were isolated and administered to inflammatory cells ex vivo, the secretion of inflammatory mediators by pathogenic vesicles was significantly suppressed. In addition, it was observed that when *Sphingomonas paucimobilis* vesicles were orally administered, the vesicles were delivered to the brain. Thus, vesicles derived from bacteria belonging to the genus *Sphingomonas* according to the present invention can be used as a method of diagnosing hepatic cirrhosis, liver cancer, myocardial infarction, renal insufficiency, diabetes, brain tumors, mild cognitive impairment, dementia, depression, autism, and atopic dermatitis, and as a composition for preventing, alleviating, or treating the diseases, such as a cosmetic, a food, or a drug, and furthermore can be expected to be usefully used as a drug carrier for delivering the drug to the brain.

MODES OF THE INVENTION

Figure 1A:
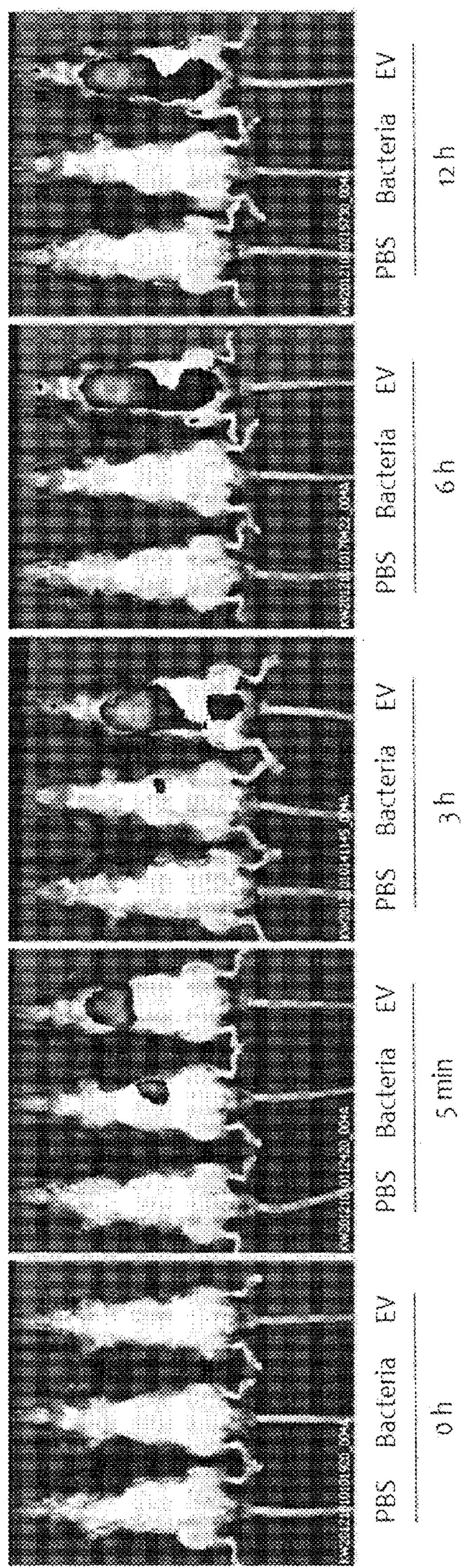
FIG. 1A is a series of photographs capturing distribution patterns of bacteria and bacteria-derived vesicles (EV) by time after the bacteria and the vesicles derived from bacteria were orally administered to mice.

The present invention relates to vesicles derived from bacteria belonging to the genus *Sphingomonas* and a use thereof.

The present inventors confirmed through metagenomic analysis that the content of vesicles derived from bacteria belonging to the genus *Sphingomonas* was remarkably reduced in samples derived from patients with hepatic cirrhosis, liver cancer, myocardial infarction, renal insufficiency, diabetes, brain tumors, mild cognitive impairment, dementia, depression, autism, and atopic dermatitis as compared to that of the samples derived from normal individuals, thereby completing the present invention based on this.

Thus, the present invention provides a method of diagnosing one or more diseases selected from the group consisting of hepatic cirrhosis, liver cancer, myocardial infarction, renal insufficiency, diabetes, brain tumors, mild cognitive impairment, dementia, depression, autism, and atopic dermatitis, or a method of providing information for diagnosis thereof, the method comprising the following steps:

(a) extracting DNAs from vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) determining a case in which a content of vesicles derived from bacteria belonging to the genus *Sphingomonas* is lower than that of the normal individual sample, as one or more diseases selected from the group consisting of hepatic cirrhosis, liver cancer, myocardial infarction, renal insufficiency, diabetes, brain tumors, mild cognitive impairment, dementia, depression, autism, and atopic dermatitis, through quantitative analysis of the PCR product.

The term "diagnosis" as used herein refers to determination of a condition of a disease of a patient over all aspects, in a broad sense. The contents of the determination are the disease entity, the etiology, the pathogenesis, the severity, the detailed aspects of a disease, the presence and absence of complications, the prognosis, and the like. The diagnosis in the present invention means determining whether hepatic cirrhosis, liver cancer, myocardial infarction, renal insufficiency, diabetes, brain tumors, mild cognitive impairment, dementia, depression, autism, or atopic dermatitis occur, the level of the disease, and the like.

The term "nanovesicle" or "vesicle" as used herein refers to a structure consisting of a nano-sized membrane secreted from various bacteria. Vesicles derived from gram-negative bacteria or outer membrane vesicles (OMVs) have endotoxins (lipopolysaccharides) or glycosphingolipid, toxic proteins, and bacterial DNA and RNA, and vesicles derived from gram-positive bacteria also have peptidoglycan and lipoteichoic acid which are cell wall components of bacteria in addition to proteins and nucleic acids. In the present invention, nanovesicles or vesicles are secreted naturally from bacteria belonging to the genus *Sphingomonas* or produced artificially by performing heat treatment, pressure treatment, or the like on the bacteria, and have an average diameter of 10 to 200 nm.

The term "metagenome" as used herein also refers to a microbiome, and refers to a total of genomes including all viruses, bacteria, fungi, and the like in an isolated region such as soil and an animal's intestines, and is typically used as a concept of genomes explaining identification of a large number of microorganisms at one time by using a sequence analyzer in order to analyze uncultivated microorganisms. In particular, the metagenome does not refer to a genome of one species, but refers to a kind of mixed genome as a genome of all species of one environmental unit. The metagenome is, when one species is defined in the development process of omics biology, a term derived from the viewpoint of making a complete species is made by various species interacting with each other as well as one kind of functionally existing species. Technically, the metagenome is an object of a technique to identify all species in one environment and investigate interactions and metabolism by analyzing all DNAs and RNAs regardless of species using a rapid sequence analysis method.

The vesicles may be isolated from a culturing solution comprising bacteria belonging to the genus *Sphingomonas* by using one or more methods selected from the group consisting of centrifugation, ultra-high speed centrifugation, high pressure treatment, extrusion, sonication, cell lysis, homogenization, freezing-thawing, electroporation, mechanical decomposition, chemical treatment, filtration by a filter, gel filtration chromatography, free-flow electrophoresis, and capillary electrophoresis. Further, a process such as washing for removing impurities and concentration of obtained vesicles may be further included.

In the present invention, the sample in Step (a) may be blood or urine, but is not limited thereto.

In the present invention, the primer pair in Step (b) may be a primer pair comprising base sequences represented by SEQ ID Nos. 1 and 2, but is not limited thereto.

As another aspect of the present invention, the present invention provides a composition for preventing, alleviating, or treating one or more diseases selected from the group consisting of hepatic cirrhosis, liver cancer, myocardial infarction, renal insufficiency, diabetes, brain tumors, mild cognitive impairment, dementia, depression, autism, and atopic dermatitis, comprising vesicles derived from bacteria belonging to the genus *Sphingomonas* as an active ingredient.

The composition comprises a pharmaceutical composition, a food composition, and a cosmetic composition.

As another aspect of the present invention, the present invention provides a method of preventing or treating one or more diseases selected from the group consisting of hepatic cirrhosis, liver cancer, myocardial infarction, renal insufficiency, diabetes, brain tumors, mild cognitive impairment, dementia, depression, autism, and atopic dermatitis, the method comprising a step of administering a composition comprising vesicles derived from bacteria belonging to the genus *Sphingomonas* as an active ingredient to a subject.

As another aspect of the present invention, the present invention provides a use of vesicles derived from bacteria belonging to the genus *Sphingomonas* for preventing or treating one or more diseases selected from the group consisting of hepatic cirrhosis, liver cancer, myocardial infarction, renal insufficiency, diabetes, brain tumors, mild cognitive impairment, dementia, depression, autism, and atopic dermatitis.

As another aspect of the present invention, the present invention provides a use of a composition comprising vesicles derived from bacteria belonging to the genus *Sphingomonas* as an active ingredient for preventing or treating one or more diseases selected from the group consisting of hepatic cirrhosis, liver cancer, myocardial infarction, renal insufficiency, diabetes, brain tumors, mild cognitive impairment, dementia, depression, autism, and atopic dermatitis.

As another aspect of the present invention, the present invention provides a use of vesicles derived from bacteria belonging to the genus *Sphingomonas* for producing a medicine used for one or more diseases selected from the group consisting of hepatic cirrhosis, liver cancer, myocardial infarction, renal insufficiency, diabetes, brain tumors, mild cognitive impairment, dementia, depression, autism, and atopic dermatitis.

As another aspect of the present invention, the present invention provides a method of delivering a drug for treating a brain disease, the method comprising administering, to a subject, a composition comprising bacteria belonging to the genus *Sphingomonas*-derived vesicles in which a drug for treating a target brain disease is loaded as an active ingredient.

As another aspect of the present invention, the present invention provides a use of vesicles derived from bacteria belonging to the genus *Sphingomonas* for delivering a drug for treating a brain disease.

The term "prevention" as used herein refers to all actions that suppress hepatic cirrhosis, liver cancer, myocardial infarction, renal insufficiency, diabetes, brain tumors, mild cognitive impairment, dementia, depression, autism, and atopic dermatitis, and the like or delay the onset thereof via administration of the composition according to the present invention.

The term "treatment" as used herein refers to all actions that alleviate or beneficially change symptoms of hepatic cirrhosis, liver cancer, myocardial infarction, renal insufficiency, diabetes, brain tumors, mild cognitive impairment, dementia, depression, autism, and atopic dermatitis, and the like via administration of composition according to the present invention.

The term "alleviation" used as used herein refers to all actions that at least reduce a parameter associated with a condition to be treated, for example, the degree of symptoms.

As used herein, the term "drug carrier" refers to all means or actions which load and deliver a drug in the composition according to the present invention in order to deliver the drug to a specific organ, tissue, cell, or organelle.

In one embodiment of the present invention, as a result of orally administering bacteria and bacteria-derived vesicles to mice and observing in vivo absorption, distribution, and excretion patterns of the bacteria and the vesicles, it was confirmed that, while the bacteria were not absorbed via the intestinal mucous membrane, the bacteria-derived vesicles were absorbed within 5 minutes after administration and systemically distributed, and excreted via the kidneys, liver, and the like (see Example 1).

In another exemplary embodiment of the present invention, it was evaluated whether bacteria and bacteria-derived vesicles directly administered to the intestines passed through the protective membrane of the mucosa, and it was confirmed that bacteria failed to pass through the protective membrane of the mucosa, whereas bacteria-derived vesicles passed through the protective membrane of the mucosa. (See Example 2).

In still another exemplary embodiment of the present invention, a bacterial metagenomic analysis was performed using vesicles isolated from the blood or urine of patients with hepatic cirrhosis, liver cancer, myocardial infarction, renal insufficiency, diabetes, brain tumors, mild cognitive impairment, dementia, depression, autism, and atopic dermatitis and normal individuals who were matched in age and sex with the patients. As a result, it was confirmed that vesicles derived from bacteria belonging to the genus *Sphingomonas* were significantly decreased in clinical samples of patients with hepatic cirrhosis, liver cancer, myocardial infarction, renal insufficiency, diabetes, brain tumors, mild cognitive impairment, dementia, depression, autism, and atopic dermatitis as compared to samples of normal individuals (see Examples 4 to 12).

In yet another exemplary embodiment of the present invention, inflammation induction effects of vesicles secreted from *Sphingomonas paucimobilis* and *Sphingomonas koreensis* strains were evaluated by culturing the strains, and as a result of comparing the secretion levels of inflammatory mediators by treating macrophages with the bacteria-derived vesicles at various concentrations, and then treating the macrophages with the *E. coli*-derived vesicles, which are pathogenic vesicles, the ability of inflammatory mediators to be secreted was remarkably reduced by the vesicles derived from bacteria belonging to the genus *Sphingomonas* as compared to the secretion of IL-6 and TNF-α by *E. coli*-derived vesicles (see Example 14).

In yet another exemplary embodiment of the present invention, anti-inflammatory effects of vesicles derived from *Sphingomonas paucimobilis* and *Sphingomonas koreensis* strains were evaluated, and as a result of evaluating the secretion of inflammatory mediators after treating macrophages with *Sphingomonas paucimobilis* and *Sphingomonas koreensis*-derived vesicles at various concentrations prior to treatment with *E. coli*-derived vesicles, which are pathogenic vesicles, it was confirmed the vesicles efficiently suppressed the secretion of IL-6 and TNF-α by inflammation-inducing *E. coli*-derived vesicles (see Examples 15 and 16).

In yet another exemplary embodiment of the present invention, it was confirmed that when *Sphingomonas paucimobilis*-derived vesicles were orally administered, the aforementioned vesicles were distributed in the stomach from the time point when 1 hour elapsed and distributed even in the small intestine and the large intestine from the time point when 3 hours elapsed, and it was confirmed that the distribution in these organs was maintained until 72 hours. Furthermore, it was confirmed that fluorescence-labeled *Sphingomonas paucimobilis*-derived vesicles moved specifically to the brain from 3 hours, and were increased until 32 hours, and then gradually decreased until the time point when 72 hours elapsed (see Example 17).

The pharmaceutical composition of the present invention may include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in the Remington's literature. The pharmaceutical composition of the present invention is not particularly limited in formulation, but may be formulated into an injection, an inhalant, an external preparation for skin, an oral ingestion, or the like.

The pharmaceutical composition of the present invention may be orally administered or may be parenterally administered (for example, administered intravenously, subcutaneously, intradermally) according to the target method, and the administration dose may vary depending on the patient's condition and body weight, severity of disease, drug form, and administration route and period, but may be appropriately selected by those of ordinary skill in the art.

The pharmaceutical composition according to the present invention is administered in a pharmaceutically effective amount. In the present invention, the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields. The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

Specifically, an effective amount of the pharmaceutical composition according to the present invention may vary depending on the age, sex, and body weight of a patient, and may be increased or decreased depending on the route of administration, severity of obesity, sex, body weight, age, and the like.

The food composition of the present invention includes a health functional food composition. The food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range.

Other ingredients are not particularly limited, except that the food composition of the present invention contains the active ingredient as an essential ingredient at the indicated ratio, and the food composition of the present invention may contain various flavorants, natural carbohydrates, and the like, like a typical beverage, as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, stevia extract (for example, rebaudioside A, glycyrrhizin and the like), and a synthetic flavorant (saccharin, aspartame and the like) may be advantageously used. The proportion of the natural carbohydrate may be appropriately determined by the choice of those of ordinary skill in the art.

The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by those of ordinary skill in the art.

The cosmetic composition of the present invention may include not only vesicles derived from bacteria belonging to the genus *Sphingomonas*, but also ingredients commonly used in cosmetic compositions, and may include, for example, general adjuvants such as an antioxidant, a stabilizer, a solubilizing agent, vitamins, pigments, and herbs, and a carrier.

In addition, the composition of the present invention may further include, in addition to the vesicles derived from bacteria belonging to the genus *Sphingomonas*, a mixture of organic UV blocking agents that have long been used within a range that does not adversely affect a skin protective effect by reaction with vesicles derived from bacteria belonging to the genus *Sphingomonas*. The organic UV blocking agent may be one or more selected from the group consisting of glyceryl PABA, drometrizole trisiloxane, drometrizole, digalloyl trioleate, disodium phenyl dibenzimidazole tetrasulfonate, diethylhexyl butamido triazone, diethylamino hydroxy benzoyl hexyl benzoate, DEA-methoxycinnamate, a mixture of lawsone and dihydroxyacetone, methylenebis-benzotriazolyltetramethylbutylphenol, 4-methylbenzylidene camphor, menthyl anthranilate, benzophenone-3(oxybenzone), benzophenone-4, benzophenone-8(dioxybenzone), butylmethoxydibenzoylmethane, bisethylhexyloxyphenol-methoxyphenyltriazine, cinoxate, ethyldihydroxypropyl PABA, octocrylene, ethylhexyldimethyl PABA, ethylhexyl-methoxycinnamate, ethylhexyl salicylate, ethylhexyl triazone, isoamyl-p-methoxycinnamate, polysilicon-15(dimethicodiethylbenzal malonate), terephthalylidene dicamphor sulfonic acid and salts thereof, TEA-salicylate, and para-aminobenzoic acid (PABA).

Examples of products to which the cosmetic composition of the present invention may be added include cosmetics such as astringents, skin softeners, nourishing toners, various creams, essences, packs, foundations, and the like, cleansings, face cleansers, soaps, treatments, beauty liquids, and the like. Particular preparations of the cosmetic composition of the present invention include a skin lotion, a skin softener, a skin toner, an astringent, a lotion, a milk lotion, a moisturizing lotion, a nourishing lotion, a massage cream, a nourishing cream, a moisturizing cream, a hand cream, an essence, a nourishing essence, a pack, a soap, a shampoo, a cleansing foam, a cleansing lotion, a cleansing cream, a body lotion, a body cleanser, an emulsion, a lipstick, a makeup base, a foundation, a press powder, a loose powder, an eye shadow, and the like.

Hereinafter, preferred Examples for helping the understanding of the present invention will be suggested. However, the following Examples are provided only to more easily understand the present invention, and the contents of the present invention are not limited by the following Examples.

EXAMPLES

Example 1

Analysis of In Vivo Absorption, Distribution, and Excretion Patterns of Bacteria and Vesicles Derived from Bacteria In order to evaluate whether bacteria and bacteria-derived vesicles were systemically absorbed through the gastrointestinal tract, an experiment was performed with the following method. First, a dose of 50 μg of each of fluorescence-labeled bacteria and bacteria-derived vesicles was orally administered to the stomach of a mouse, and fluorescence was measured after 0 minute, 5 minutes, 3 hours, 6 hours, and 12 hours. As a result of observing the entire image of the mouse, as illustrated in FIG. 1A, the bacteria were not systemically absorbed, but the vesicles derived from bacteria were systemically absorbed 5 minutes after administration, and fluorescence was strongly observed in the bladder 3 hours after administration, so that it could be seen that the vesicles were excreted to the urinary tract. Further, it could be seen that the vesicles were present in the body until 12 hours after administration (see FIG. 1A).

Figure 1B:
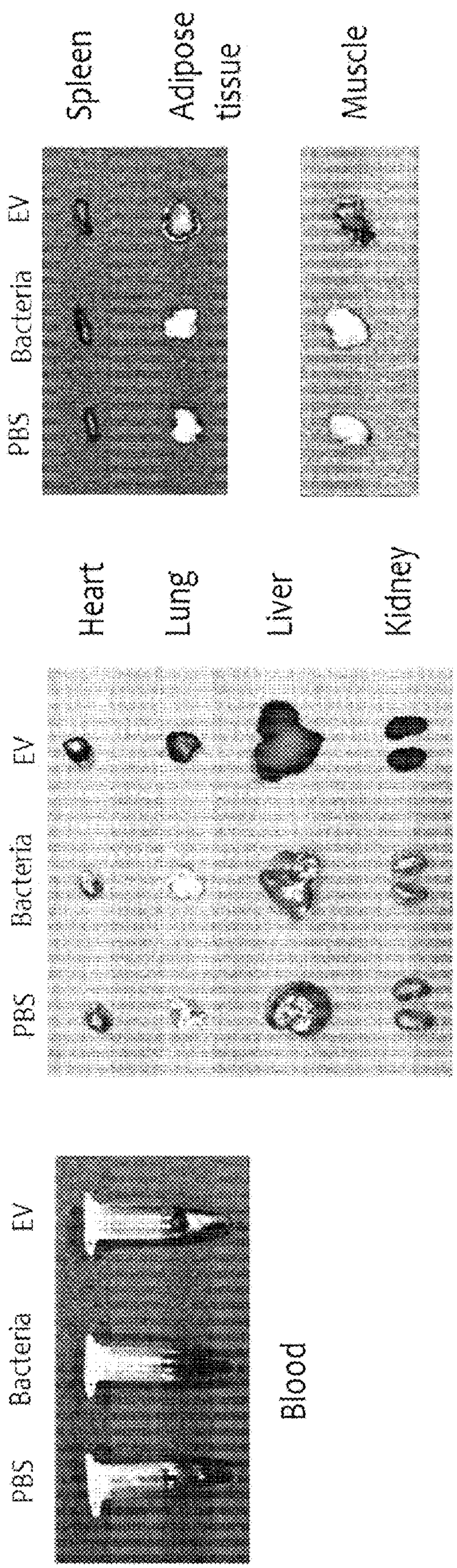
FIG. 1B is a result of evaluating the in vivo distribution patterns of the bacteria and the vesicles by harvesting blood, kidneys, liver, and various organs at 12 hours after orally administering the bacteria and the vesicles.

In order to evaluate the pattern in which the bacteria and the vesicles derived from the bacteria infiltrated into various organs after they were systemically absorbed, 50 μg of bacteria and vesicles derived from bacteria labeled with fluorescence were administered in the same manner as described above, and then the blood, heart, lungs, liver, kidneys, spleen, fat, and muscle were collected 12 hours after administration. As a result of observing fluorescence in the collected tissues, as illustrated in FIG. 1B, it could be seen that the vesicles derived from bacteria were distributed in the blood, heart, lungs, liver, spleen, fat, muscle, and kidneys but the bacteria were not absorbed (see FIG. 1B).

Example 2

Evaluation of Whether Bacteria and Bacteria-Derived Vesicles Penetrate Protective Membrane of Intestinal Mucosa In order to evaluate whether bacteria and bacteria-derived vesicles passed through the protective membrane of the mucosa to be infiltrated into tissue, after bacteria and bacteria-derived vesicles were directly administered to the intestines, infiltration into the intestinal tissue after passing through the protective membrane of the mucosa was evaluated by an immunohistochemistry method. In order to evaluate the presence of bacteria and vesicles in the mucosal tissue, antibodies against the bacteria and the vesicles were prepared, attached to a green fluorescent protein (GFP) and used, and after staining with 4,6-diamidino 2-phenylindole (DAPI), observed under a microscope.

Figure 2:
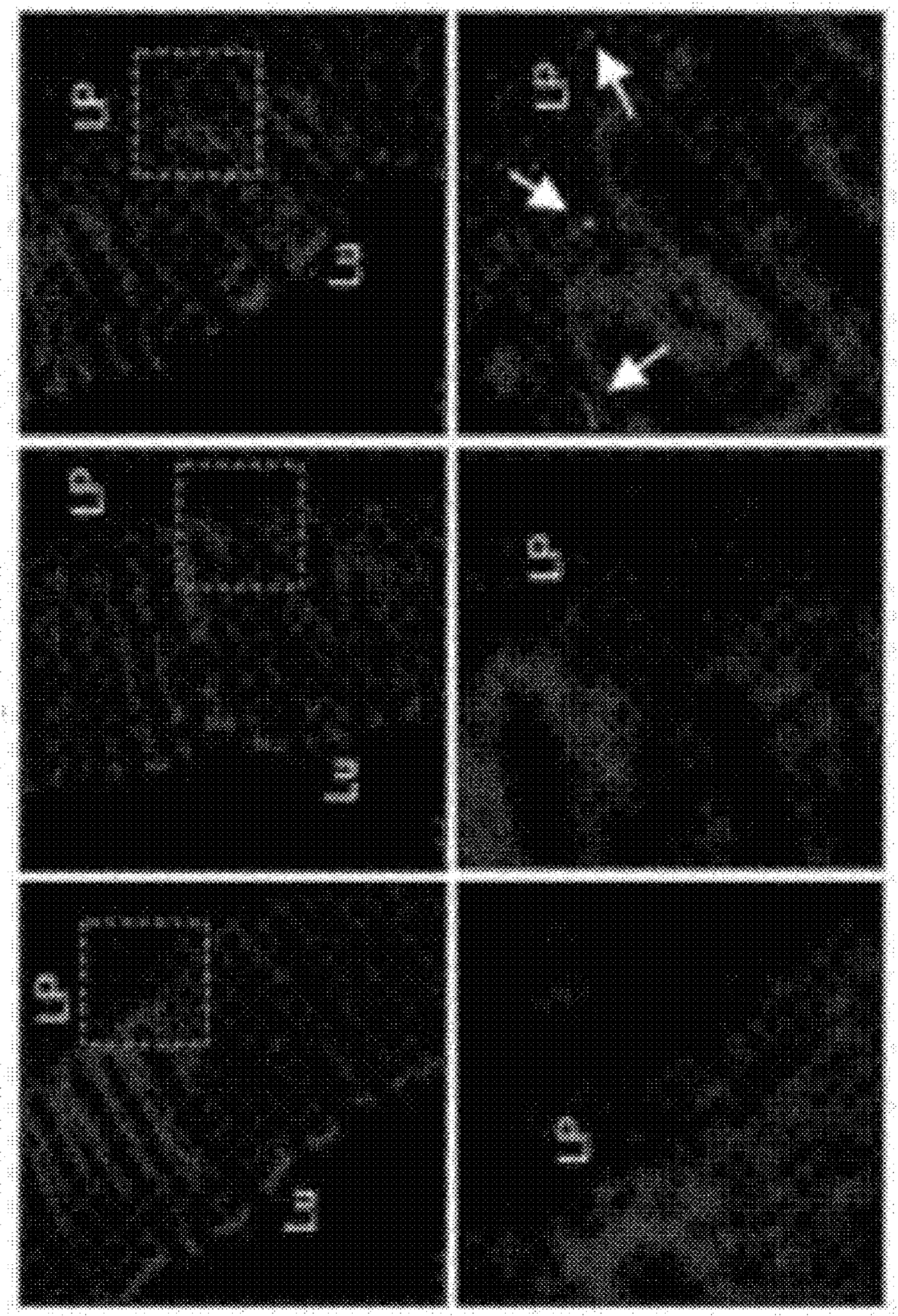
FIG. 2 is a view of evaluating whether bacteria and bacteria-derived vesicles (EV) are infiltrated into intestinal mucosal epithelial cells after administering the bacteria and bacteria-derived vesicles to the intestine of a mouse (Lu, gut lumen; LP, gut lamina propria).

As a result, it was confirmed that bacteria failed to pass through the protective membrane of the mucosa, whereas bacteria-derived vesicles passed through the mucosa and infiltrated into the intestinal tissue (see FIG. 2).

Example 3

Metagenomic Analysis of Vesicles Derived from Bacteria in Clinical Sample

After blood or urine was first put into a 10-ml tube and suspended matter was allowed to settle by a centrifuge (3,500×g, 10 min, 4° C.), only the supernatant was transferred to a new 10-ml tube. After bacteria and impurities were removed by using a 0.22-μm filter, they were transferred to a Centriprep tube (centrifugal filters 50 kD) and centrifuged at 1,500×g and 4° C. for 15 minutes, materials smaller than 50 kD were discarded, and the residue was concentrated to 10 ml. After bacteria and impurities were removed once again by using a 0.22-μm filter, the supernatant was discarded by using a ultra-high speed centrifugation at 150,000×g and 4° C. for 3 hours with a Type 90Ti rotor, and an aggregated pellet was dissolved in physiological saline (PBS).

Internal DNA was extracted out of the lipid by boiling 100 μl of the vesicles isolated by the above method at 100° C., and then cooled on ice for 5 minutes. And then, in order to remove the remaining suspended matter, the DNA was centrifuged at 10,000×g and 4° C. for 30 minutes, and only the supernatant was collected. And, the amount of DNA was quantified by using Nanodrop. Thereafter, in order to confirm whether the DNA derived from bacteria was present in the extracted DNA, PCR was performed with 16s rDNA primers shown in the following Table 1 and it was confirmed that genes derived from bacteria were present in the extracted genes.

TABLE 1

| primer | | Sequence | SEQ ID No. |
| --- | --- | --- | --- |
| 16SrDNA | 16S_ V3_F | 5'- TCGTCGGCAGCGTCAGATGTGTATAAGA GACAGCCTACGGGNGGCWGCAG-3' | 1 |
| | 16S_ V4_R | 5'- GTCTCGTGGGCTCGGAGATGTGTATAAG AGACAGGACTACHVGGGTATCTAATCC | 2 |

The DNA extracted by the above method was amplified using the 16S rDNA primers, and then sequencing was performed (Illumina MiSeq sequencer), the results were output as a standard flowgram format (SFF) file, the SFF file was converted into a sequence file (.fasta) and a nucleotide quality score file using GS FLX software (v2.9), and then the reliability estimation for the reads was confirmed, and a portion in which the window (20 bps) average base call accuracy was less than 99% (Phred score<20) was removed. For the OTU (operational taxonomy unit) analysis, clustering was performed according to sequence similarity by using UCLUST and USEARCH, the genus, family, order, class, and phylum were clustered based on 94%, 90%, 85%, 80%, and 75% sequence similarity, respectively, classification was performed at the phylum, class, order, family, and genus levels of each OUT, and bacteria having a sequence similarity of 97% or more at the genus level were profiled by using the 16S RNA sequence database (108,453 sequences) of BLASTN and GreenGenes (QIIME).

Example 4

Figure 3:
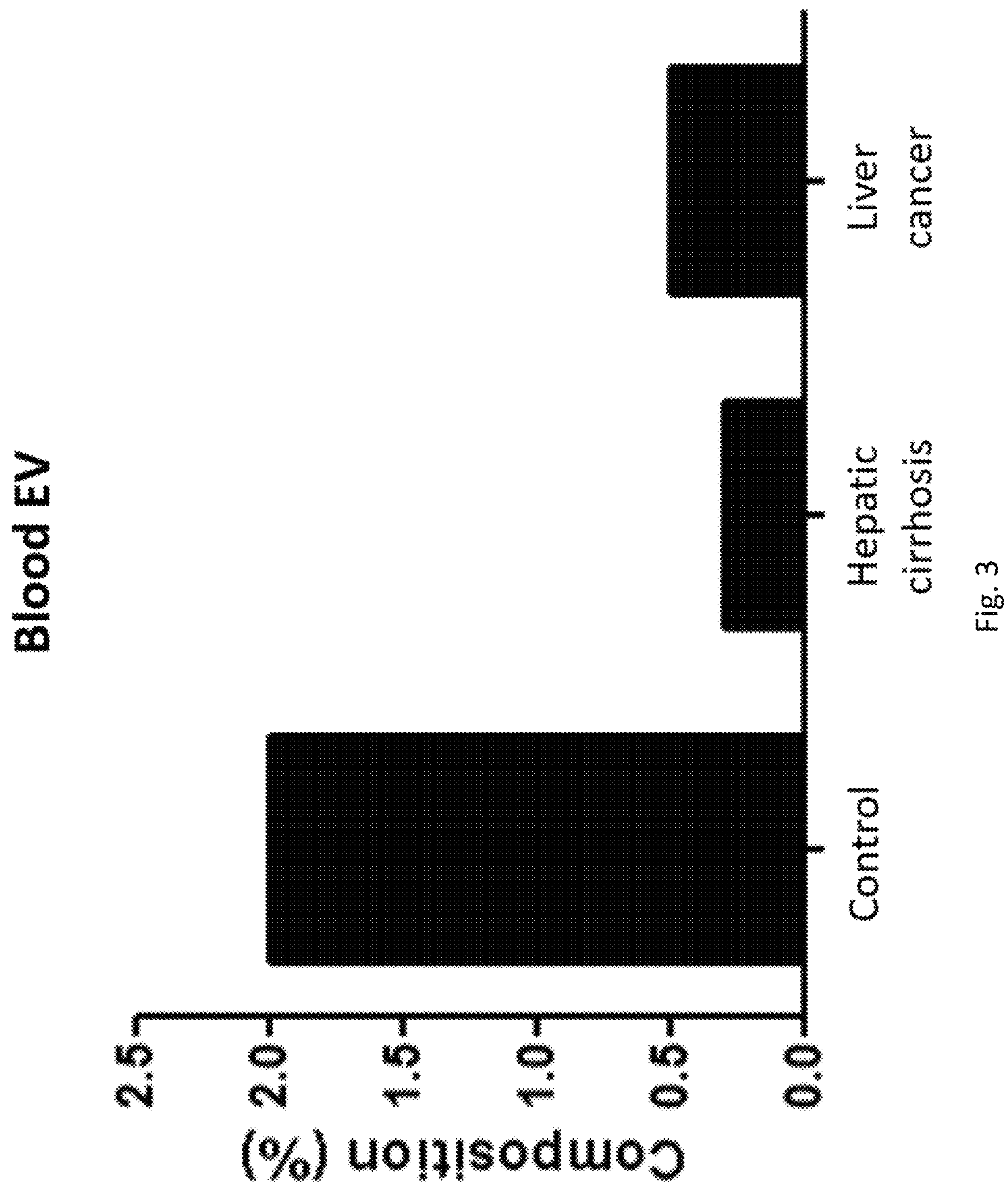
FIG. 3 is a result of comparing the distributions of vesicles derived from bacteria belonging to the genus *Sphingomonas* after metagenomic analysis of bacteria-derived vesicles present in the blood of hepatic cirrhosis patients, liver cancer patients and a normal individuals.

Metagenomic Analysis of Bacteria-Derived Vesicles in Blood of Patient with Liver Disease After a metagenomic analysis was performed using the method of Example 3 on the blood from 97 patients with hepatic cirrhosis, 76 patients with liver cancer, and 171 normal individuals who were matched in age and sex by extracting genes from vesicles present in the blood, the distribution of vesicles derived from bacteria belonging to the genus *Sphingomonas* was evaluated. As a result, it was confirmed that vesicles derived from belonging to the genus *Sphingomonas* were significantly decreased in the blood from the patients with hepatic cirrhosis and liver cancer as compared to the blood from the normal individuals (see FIG. 3).

Example 5

Figure 4:
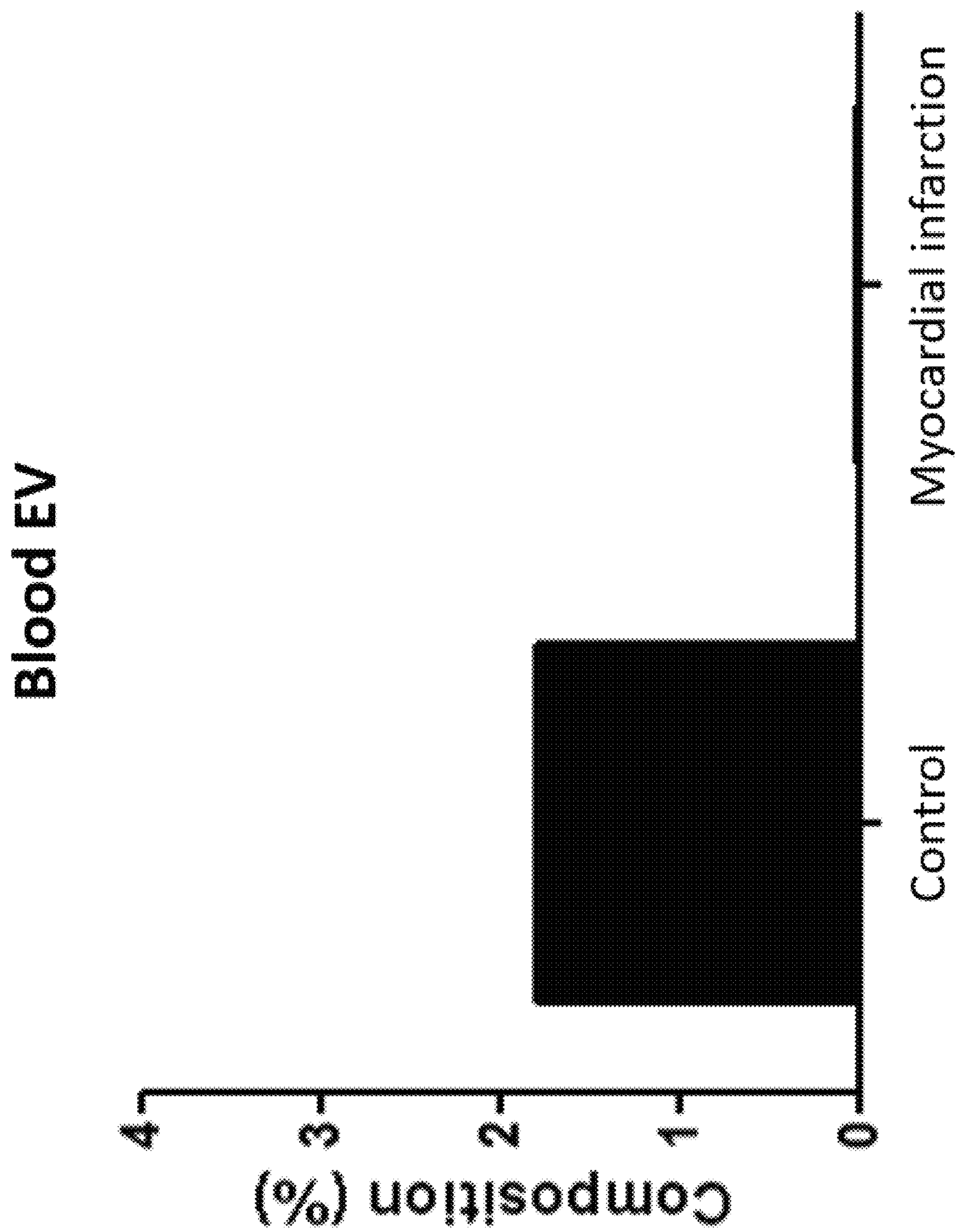
FIG. 4 is a result of comparing the distributions of vesicles derived from bacteria belonging to the genus *Sphingomonas* after metagenomic analysis of bacteria-derived vesicles present in the blood of myocardial infarction patients and a normal individuals.

Metagenomic Analysis of Bacteria-Derived Vesicles in Blood of Patient with Myocardial Infarction After a metagenomic analysis was performed using the method of Example 3 on the blood from 69 patients with myocardial infarction and 159 normal individuals who were matched in age and sex by extracting genes from vesicles present in the blood, the distribution of vesicles derived from bacteria belonging to the genus *Sphingomonas* was evaluated. As a result, it was confirmed that vesicles derived from belonging to the genus *Sphingomonas* were significantly decreased in the blood from the patients with myocardial infarction as compared to the blood from the normal individuals (see FIG. 4).

Example 6

Figure 5:
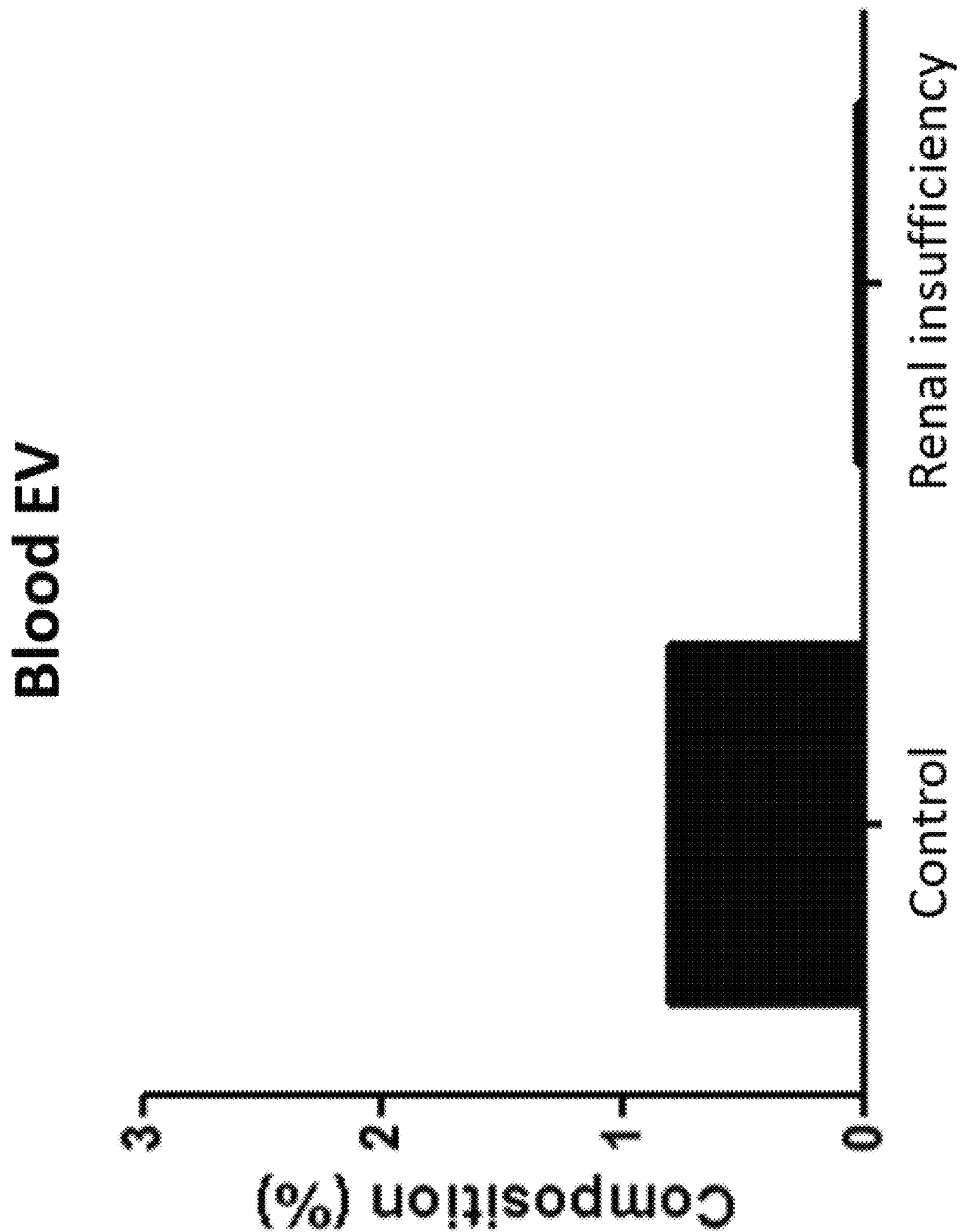
FIG. 5 is a result of comparing the distributions of vesicles derived from bacteria belonging to the genus *Sphingomonas* after metagenomic analysis of bacteria-derived vesicles present in the blood of renal insufficiency patients and a normal individuals.

Metagenomic Analysis of Bacteria-Derived Vesicles in Blood of Patient with Renal Insufficiency After a metagenomic analysis was performed using the method of Example 3 on the blood from 36 patients with renal insufficiency and 72 normal individuals who were matched in age and sex by extracting genes from vesicles present in the blood, the distribution of vesicles derived from bacteria belonging to the genus *Sphingomonas* was evaluated. As a result, it was confirmed that vesicles derived from belonging to the genus *Sphingomonas* were significantly decreased in the blood from the patients with renal insufficiency as compared to the blood from the normal individuals (see FIG. 5).

Example 7

Figure 6:
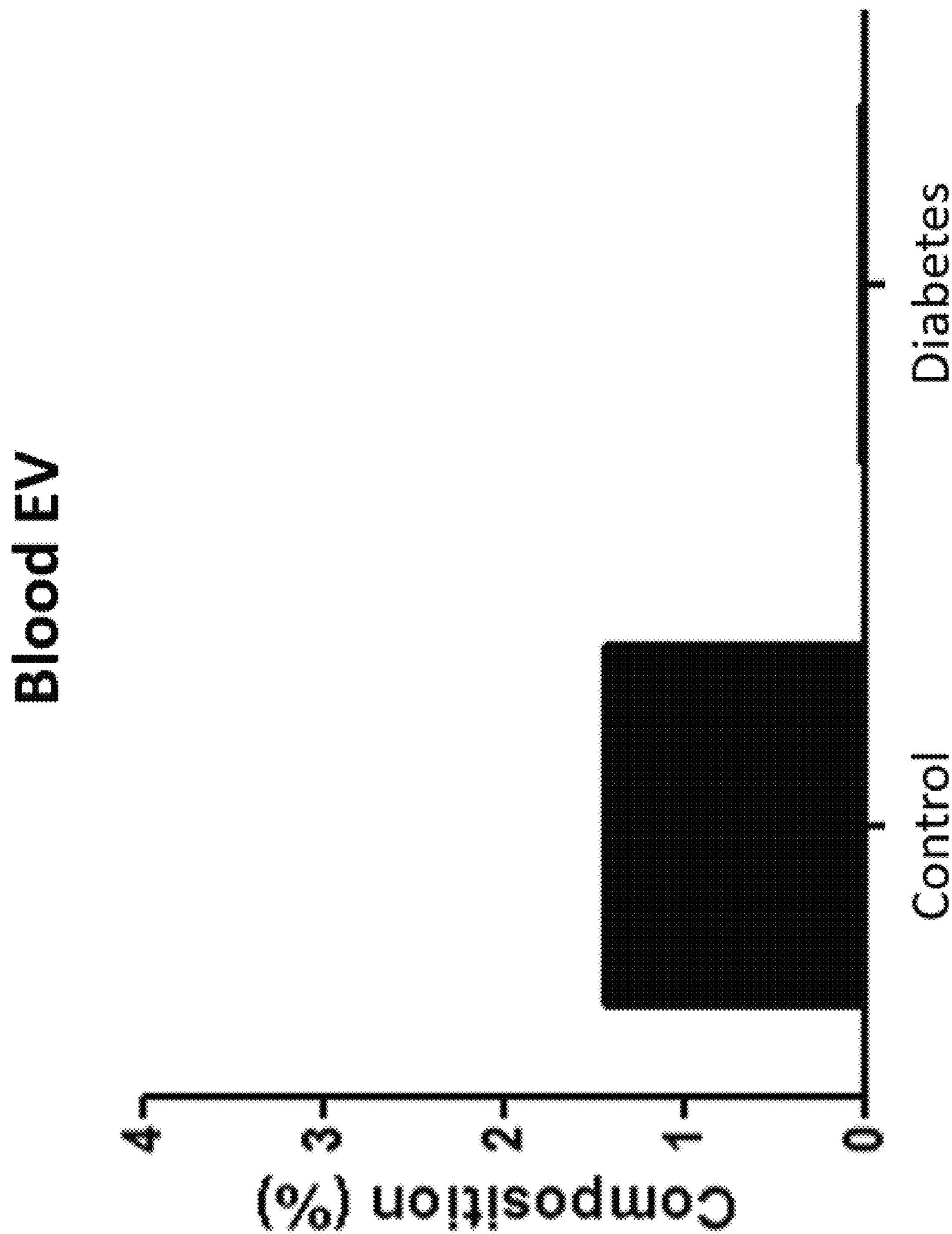
FIG. 6 is a result of comparing the distributions of vesicles derived from bacteria belonging to the genus *Sphingomonas* after metagenomic analysis of bacteria-derived vesicles present in the blood of diabetes patients and a normal individuals.

Metagenomic Analysis of Bacteria-Derived Vesicles in Blood of Patient with Diabetes After a metagenomic analysis was performed using the method of Example 3 on the blood from 81 patients with diabetes and 126 normal individuals who were matched in age and sex by extracting genes from vesicles present in the blood, the distribution of vesicles derived from bacteria belonging to the genus *Sphingomonas* was evaluated. As a result, it was confirmed that vesicles derived from belonging to the genus *Sphingomonas* were significantly decreased in the blood from the patients with diabetes as compared to the blood from the normal individuals (see FIG. 6).

Example 8

Figure 7:
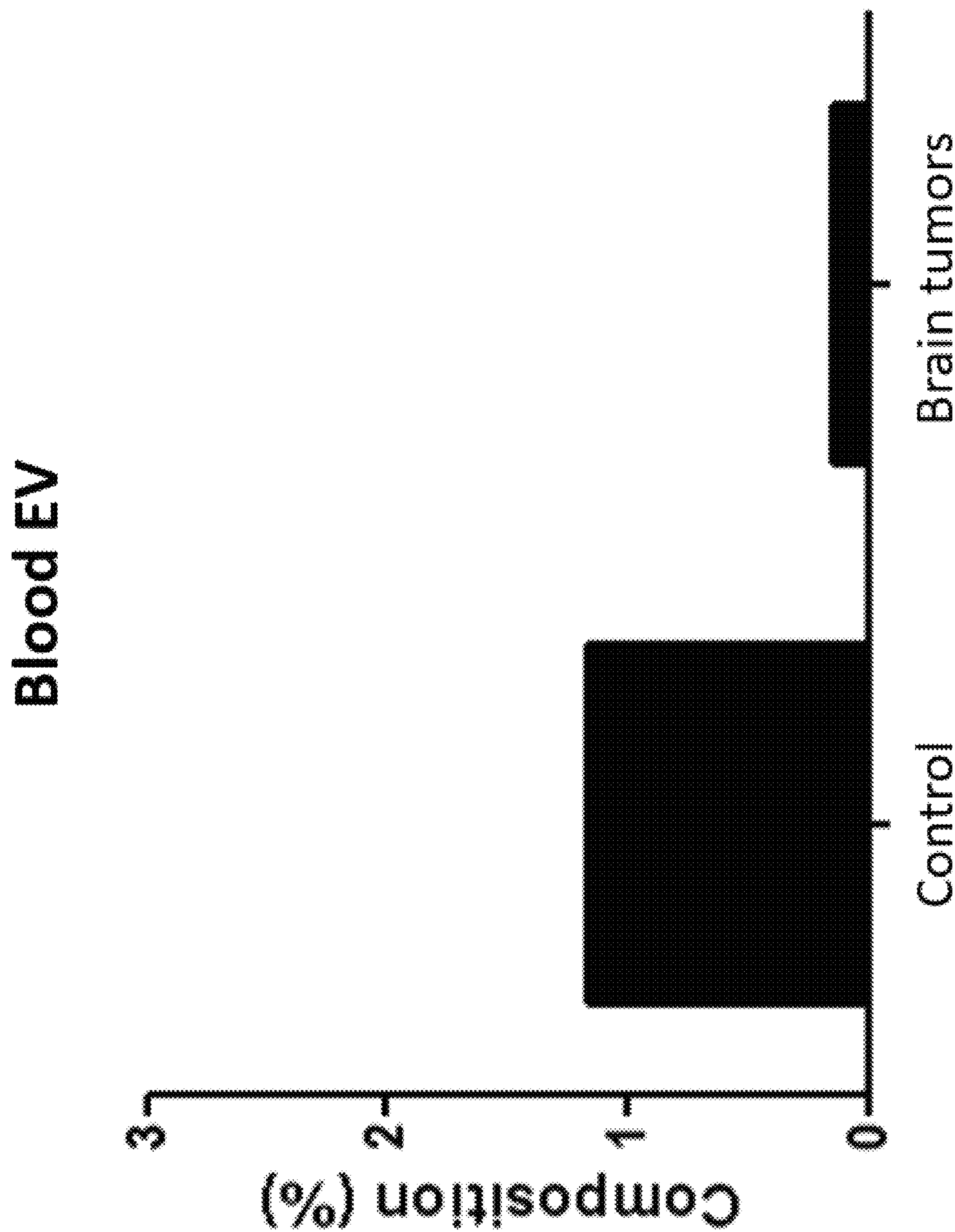
FIG. 7 is a result of comparing the distributions of vesicles derived from bacteria belonging to the genus *Sphingomonas* after metagenomic analysis of bacteria-derived vesicles present in the blood of brain tumors patients and a normal individuals.

Metagenomic Analysis of Bacteria-Derived Vesicles in Blood of Patient with Brain Tumors After a metagenomic analysis was performed using the method of Example 3 on the blood from 80 patients with brain tumors and 121 normal individuals who were matched in age and sex by extracting genes from vesicles present in the blood, the distribution of vesicles derived from bacteria belonging to the genus *Sphingomonas* was evaluated. As a result, it was confirmed that vesicles derived from belonging to the genus *Sphingomonas* were significantly decreased in the blood from the patients with brain tumors as compared to the blood from the normal individuals (see FIG. 7).

Example 9

Figure 8:
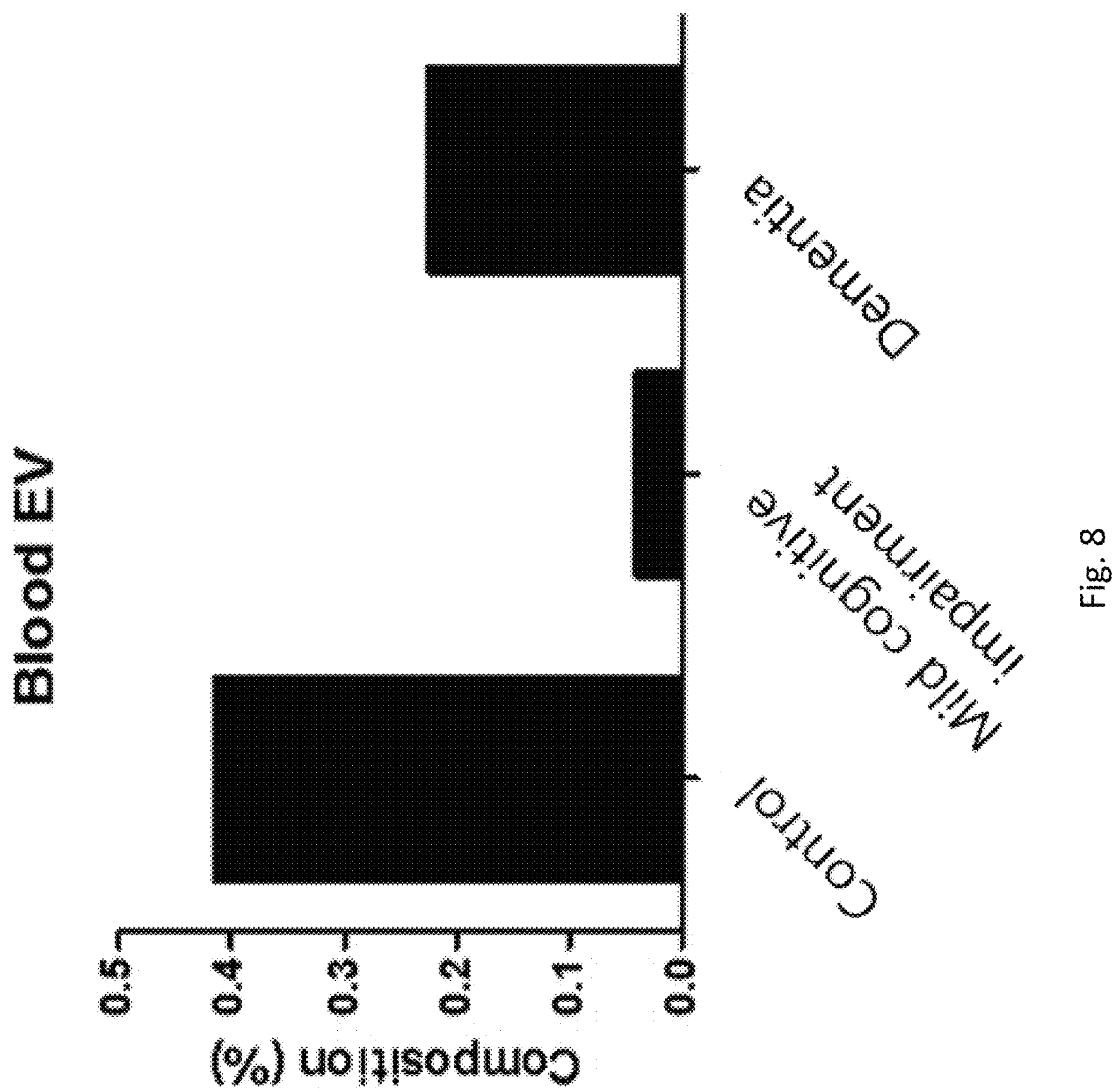
FIG. 8 is a result of comparing the distributions of vesicles derived from bacteria belonging to the genus *Sphingomonas* after metagenomic analysis of bacteria-derived vesicles present in the blood of mild cognitive impairment patients, Alzheimer's dementia patients and a normal individuals.

Metagenomic Analysis of Bacteria-Derived Vesicles in Blood of Patient with Mild Cognitive Impairment and Dementia After a metagenomic analysis was performed using the method of Example 3 on the blood from 76 patients with mild cognitive impairment, 70 patients with Alzheimer's dementia, and 146 normal individuals who were matched in age and sex by extracting genes from vesicles present in the blood, the distribution of vesicles derived from bacteria belonging to the genus *Sphingomonas* was evaluated. As a result, it was confirmed that vesicles derived from belonging to the genus *Sphingomonas* were significantly decreased in the blood from the patients with mild cognitive impairment and Alzheimer's dementia as compared to the blood from the normal individuals (see FIG. 8).

Example 10

Figure 9:
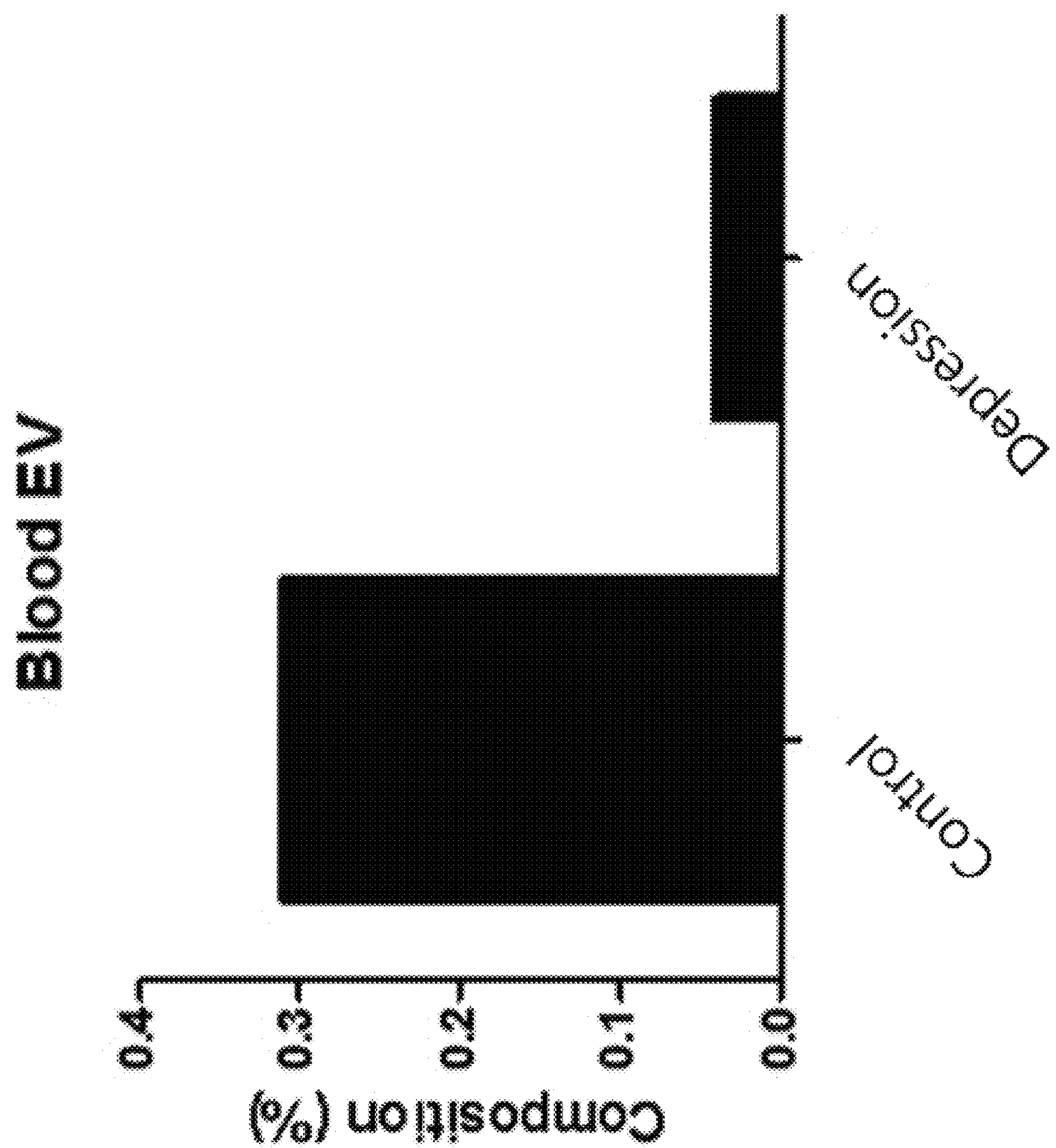
FIG. 9 is a result of comparing the distributions of vesicles derived from bacteria belonging to the genus *Sphingomonas* after metagenomic analysis of bacteria-derived vesicles present in the blood of depression patients and a normal individuals.

Metagenomic Analysis of Bacteria-Derived Vesicles in Blood of Patient with Depression After a metagenomic analysis was performed using the method of Example 3 on the blood from 70 patients with depression and 140 normal individuals who were matched in age and sex by extracting genes from vesicles present in the blood, the distribution of vesicles derived from bacteria belonging to the genus *Sphingomonas* was evaluated. As a result, it was confirmed that vesicles derived from belonging to the genus *Sphingomonas* were significantly decreased in the blood from the patients with depression as compared to the blood from the normal individuals (see FIG. 9).

Example 11

Figure 10:
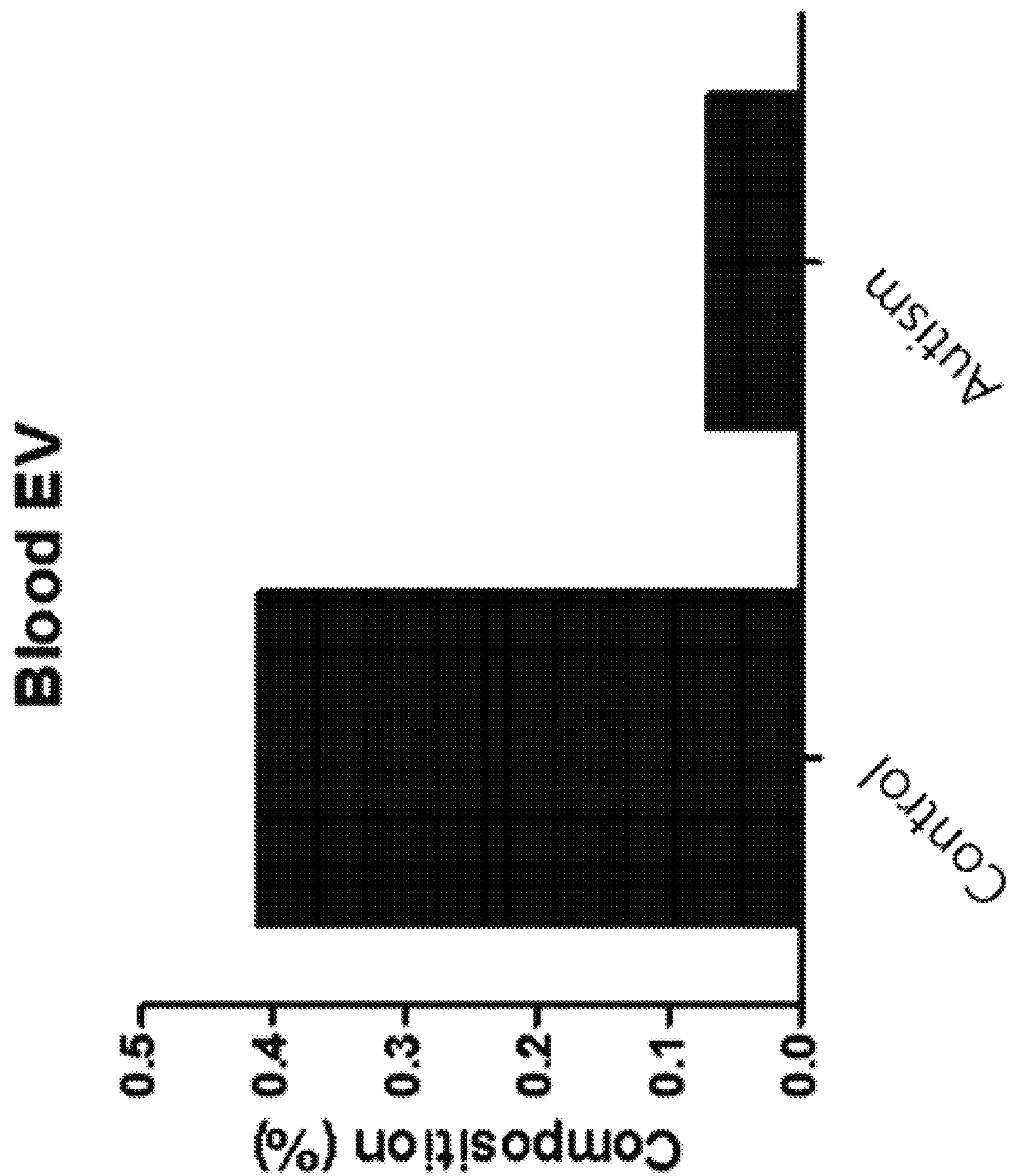
FIG. 10 is a result of comparing the distributions of vesicles derived from bacteria belonging to the genus *Sphingomonas* after metagenomic analysis of bacteria-derived vesicles present in the urine of autism patients and a normal individuals.

Metagenomic Analysis of Bacteria-Derived Vesicles in Urine of Patient with Autism After a metagenomic analysis was performed using the method of Example 3 on the urine from 30 patients with autism and 40 normal individuals who were matched in age and sex by extracting genes from vesicles present in the urine, the distribution of vesicles derived from bacteria belonging to the genus *Sphingomonas* was evaluated. As a result, it was confirmed that vesicles derived from belonging to the genus *Sphingomonas* were significantly decreased in the urine from the patients with autism as compared to the urine from the normal individuals (see FIG. 10).

Example 12

Figure 11:
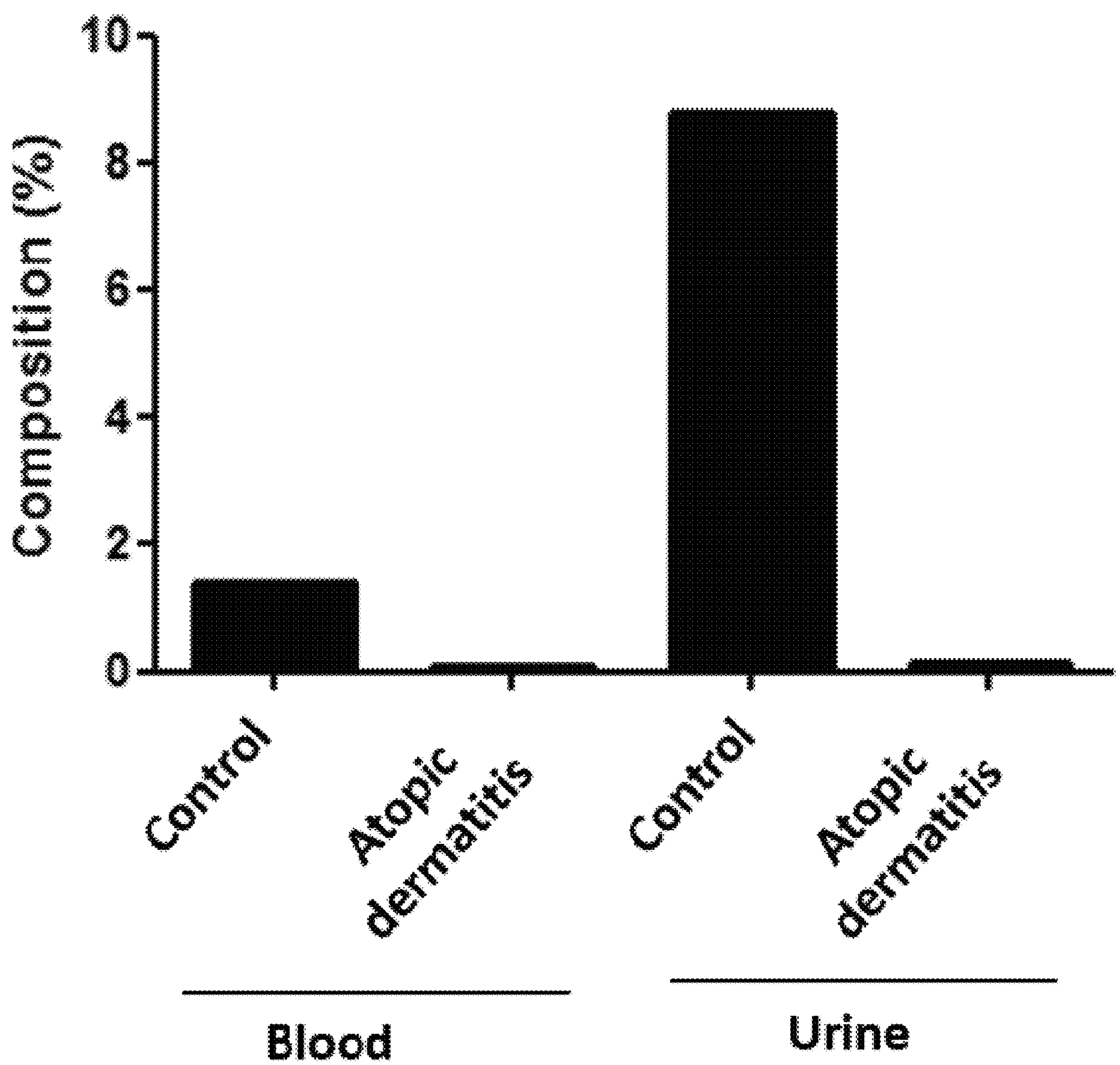
FIG. 11 is a result of comparing the distributions of vesicles derived from bacteria belonging to the genus *Sphingomonas* after metagenomic analysis of bacteria-derived vesicles present in the blood and urine of atopic dermatitis patients and a normal individuals.

Metagenomic Analysis of Bacteria-Derived Vesicles in Blood and Urine of Patient with Atopic Dermatitis After a metagenomic analysis was performed using the method of Example 3 on the blood and urine from 61 patients with atopic dermatitis and 52 normal individuals who were matched in age and sex by extracting genes from vesicles present in the blood and urine, the distribution of vesicles derived from bacteria belonging to the genus *Sphingomonas* was evaluated. As a result, it was confirmed that vesicles derived from belonging to the genus *Sphingomonas* were significantly decreased in the blood and urine from the patients with atopic dermatitis as compared to the blood and urine from the normal individuals (see FIG. 11).

Example 13

Isolation of Vesicles from *Sphingomonas Paucimobilis* and *Sphingomonas Koreensis* Culturing Solution Based on the above examples, a *Sphingomonas paucimobilis* and a *Sphingomonas koreensis* strain were cultured, and then vesicles were isolated therefrom and characteristics of the isolated vesicles were analyzed. The strains were cultured in a de Man-Rogosa and Sharpe (MRS) medium in an incubator at 37° C. until the absorbance (OD 600) became 1.0 to 1.5, and then sub-cultured in a Luria-Bertani (LB) medium. Subsequently, a culture supernatant including the strain was recovered and centrifuged at 10,000×g and 4□ for 20 minutes, and then the strain was removed and filtered through a 0.22 μm filter. The filtered supernatant was concentrated to a volume of less than or equal to 50 ml through microfiltration by using a MasterFlex pump system (Cole-Parmer, US) with a 100 kDa Pellicon 2 Cassette filter membrane (Merck Millipore, US). The concentrated supernatant was filtered once again with a 0.22-μm filter. Thereafter, proteins were quantified by using a BCA assay, and the following experiments were performed on the obtained vesicles.

Example 14

Inflammation-Inducing Effect of *Sphingomonas Paucimobilis*-Derived Vesicles

To examine an effect of *Sphingomonas paucimobilis*-derived vesicles (*Sphingomonas paucimobilis* EV, SPC101) on the secretion of inflammatory mediators (IL-6 and TNF-α) in inflammatory cells, Raw 264.7 cells, which is a mouse macrophage line, were treated with *Sphingomonas paucimobilis*-derived vesicles at various concentrations (0.1, 1, or 10 μg/ml), followed by apoptosis and ELISA.

More specifically, Raw 264.7 cells aliquoted at $5\times10^4$ cells/well into a 48-well cell culture plate were treated with *Sphingomonas paucimobilis*-derived vesicles at various concentrations, which were diluted with a DMEM (Dulbecos Modified Eagles Medium) serum-free medium, and the treated cells were cultured for 12 hours. Thereafter, apoptosis was measured by using EZ-CYTOX (Dogen, Korea), the cell culture solution was collected in a 1.5-ml tube and centrifuged at 3,000 g for 5 minutes, the supernatant was recovered and stored at −80° C., and then an ELISA analysis was performed.

For ELISA, a capture antibody was diluted with phosphate buffered saline (PBS) and 50 μl aliquots thereof were dispensed into a 96-well polystyrene plate in accordance with a working concentration, and then allowed to react at 4□ overnight. Subsequently, the sample was washed three times with 100 μl of a PBST (0.05% Tween-20-containing PBS) solution, and then an RD (1% bovine serum albumin (BSA)-containing PBS) solution was dispensed in 100 μl aliquots, followed by blocking at room temperature for 1 hour, and then the sample and a standard were dispensed in 50 μl aliquots in accordance with concentration and allowed to react at room temperature for 2 hours. Then, the sample and the standard were washed three times with 100 μl of PBST, and then the detection antibody was diluted with RD, and the diluted solution was dispensed in 50 μl aliquots in accordance with a working concentration and allowed to react at room temperature for 2 hours. Thereafter, the sample and the standard were washed three times with 100 μl of PBST, and then streptavidin-horseradish peroxidase (HRP) (R&D Systems, USA) was diluted in RD to 1/40, and the diluted solution was dispensed in 50 μl aliquots and allowed to react at room temperature for 20 minutes.

Lastly, the sample and the standard were washed three times with 100 μl of PBST, and then a 3,3',5,5'-tetramethylbenzidine (TMB) substrate (SurModics, USA) was dispensed in 50 μl aliquots, and then when color was developed after 5 minutes to 20 minutes, a 1M sulfuric acid solution was dispensed in 50 μl aliquots, thereby stopping the reaction, and absorbance at 450 nm was measured using a SpectraMax M3 microplate reader (Molecular Devices, USA).

Figure 12:
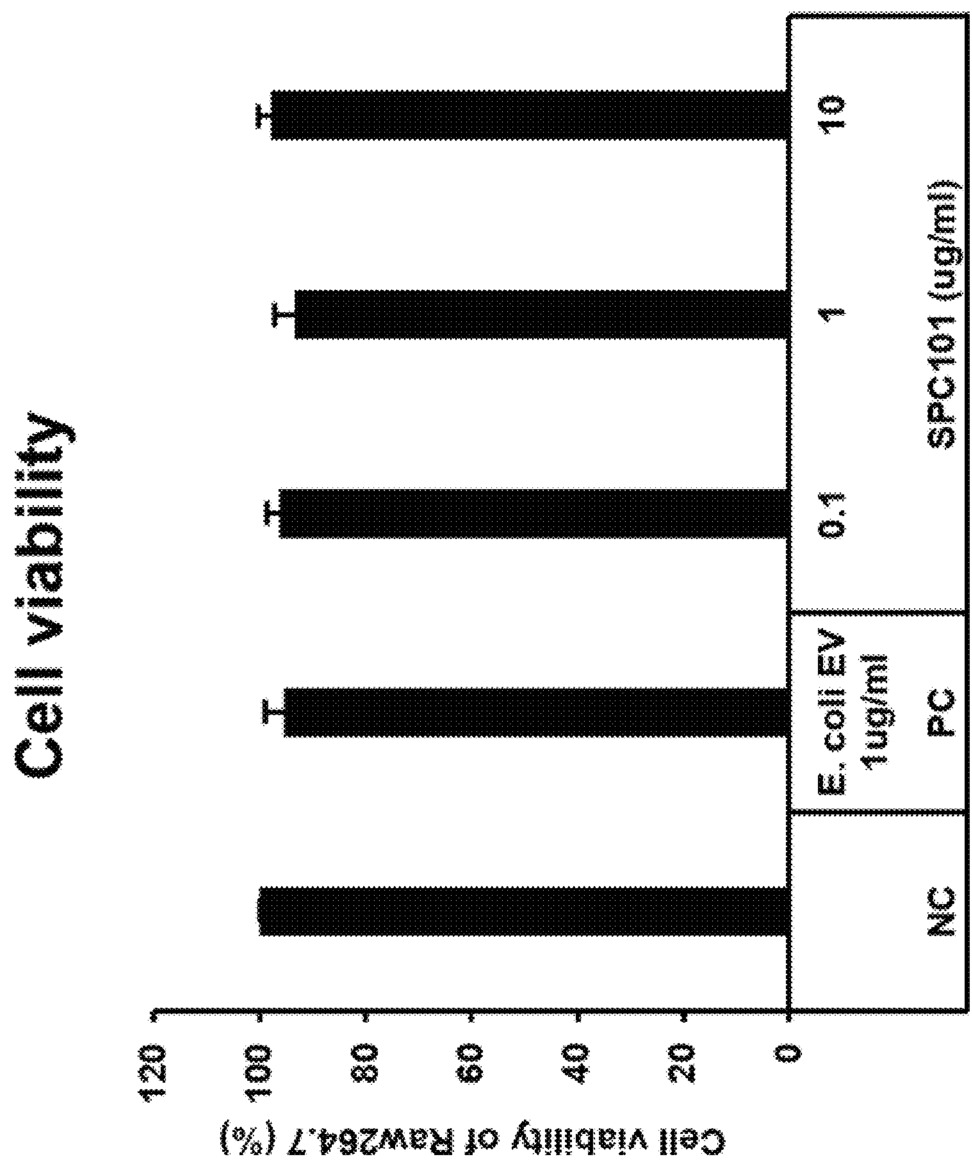
FIG. 12 is a result of evaluating apoptosis by treating microphages (Raw264.7 cells) with *Sphingomonas paucimobilis*-derived vesicles in order to evaluate the apoptotic effects of *Sphingomonas paucimobilis*-derived vesicles (EV, extracellular vesicle).
Figure 13A:
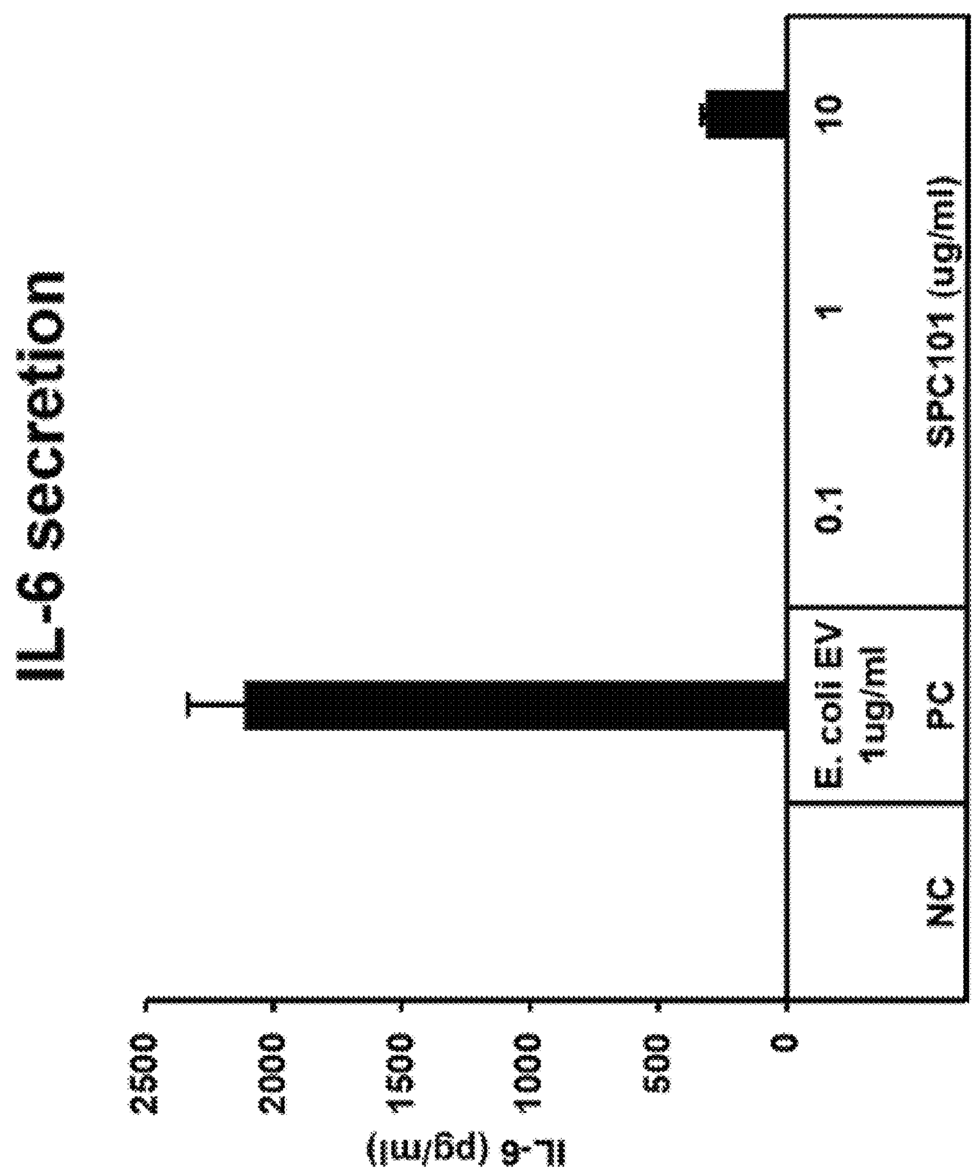
FIGS. 13A and 13B are results of comparing the secretion level of inflammatory mediators with that of *E. coli* EV which is a pathogenic vesicle by treating macrophages (Raw264.7 cells) with *Sphingomonas paucimobilis*-derived vesicles in order to evaluate the inflammation induction effects of *Sphingomonas paucimobilis*-derived vesicles, FIG. 13A compares the secretion levels of IL-6, and FIG. 13B compares the secretion levels of TNF-α (EV: extracellular vesicle).
Figure 13B:
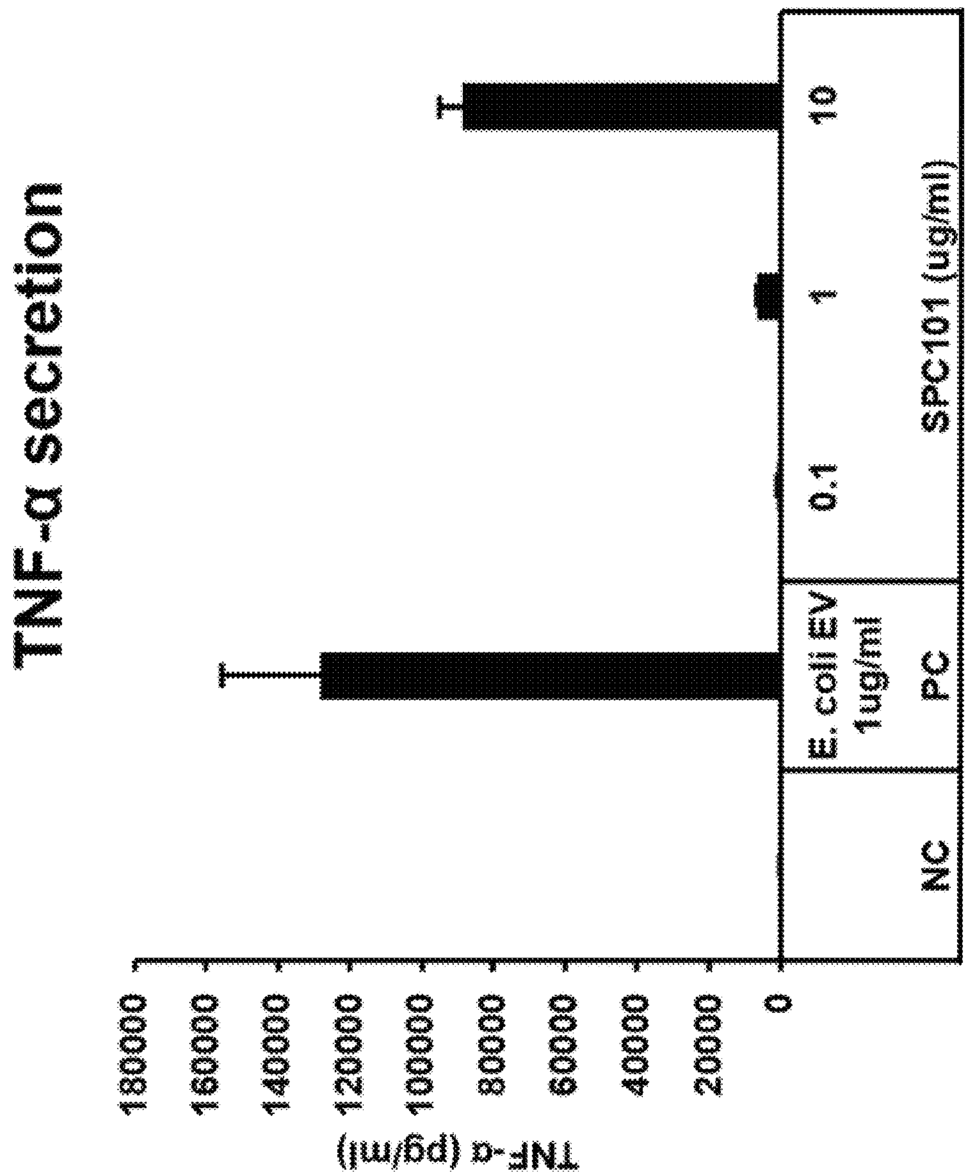

As a result, as illustrated in FIG. 12, apoptosis due to the treatment with *Sphingomonas paucimobilis*-derived vesicles (SPC 101) was not observed (see FIG. 12). Further, as a result of evaluating the secretion pattern of inflammatory mediators in inflammatory cells, it was confirmed that the secretion of inflammatory mediators such as IL-6 (FIG. 13A) and TNF-α (FIG. 13B) was much reduced upon treatment with *Sphingomonas paucimobilis*-derived vesicles (SPC 101) compared to upon treatment with *E. coli*-derived vesicles (*E. coli* EV 1 μg/ml), which are a positive control (see FIGS. 13A and 13B).

Example 15

Anti-Inflammatory Effects of *Sphingomonas Paucimobilis*-Derived Vesicles

In order to evaluate the anti-inflammatory effects of *Sphingomonas paucimobilis*-derived vesicles based on the result of Example 14, after mouse macrophage cell lines were pre-treated with *Sphingomonas paucimobilis*-derived vesicles (SPC 101) at various concentrations (0.1, 1, and 10 μg/ml) for 12 hours, the cell lines were treated with 1 μg/ml of *E. coli*-derived vesicles, which are a pathogenic factor, and then the secretion of inflammatory cytokines was measured by ELISA after 12 hours.

Figure 14A:
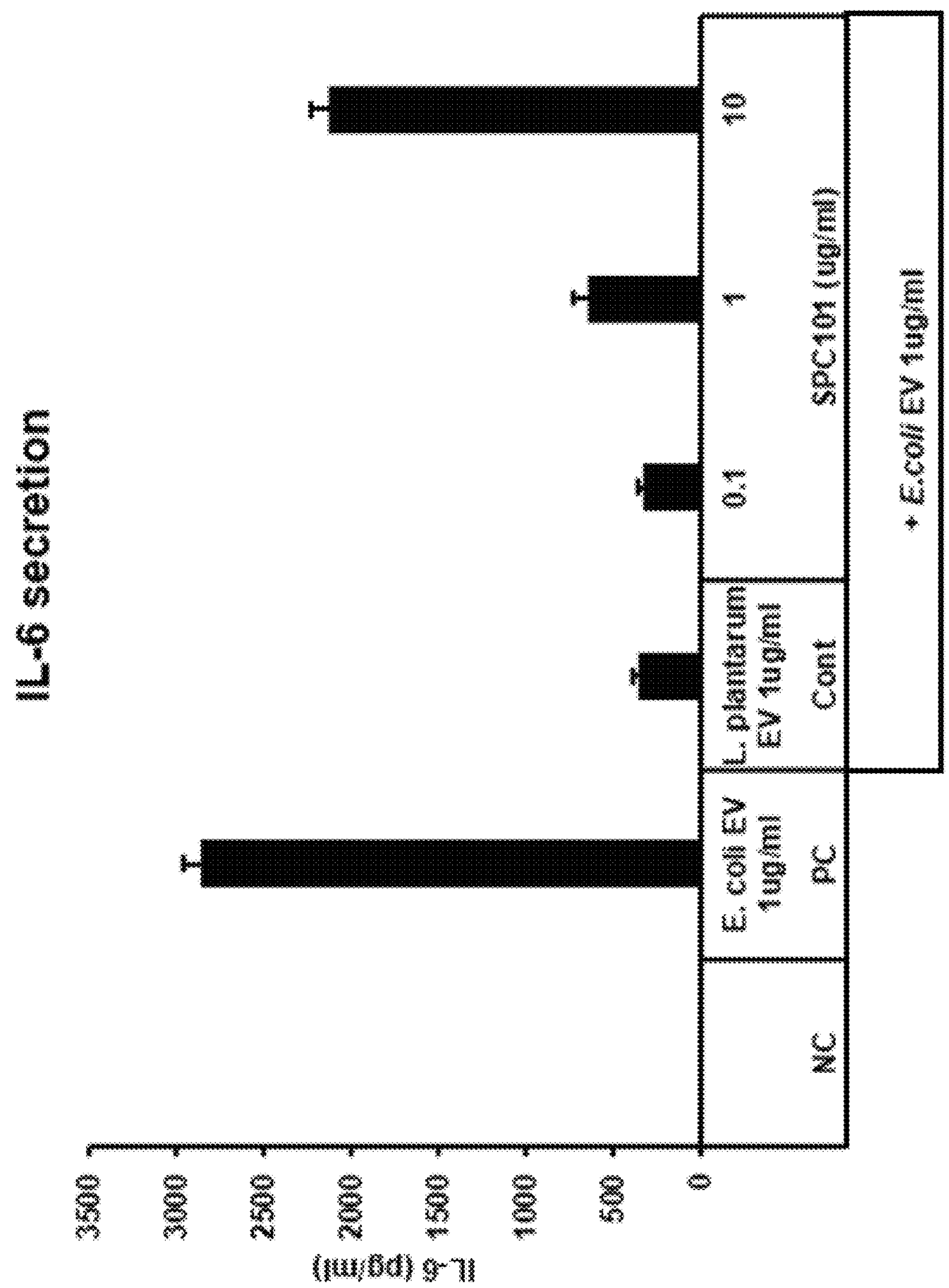
FIGS. 14A and 14B are results of evaluating effects of *E. coli* EV on the secretion of inflammatory mediators by pretreatment with *Sphingomonas paucimobilis*-derived vesicles prior to treatment with *E. coli* EV which is a pathogenic vesicle in order to evaluate the anti-inflammatory effects of *Sphingomonas paucimobilis*-derived vesicles, FIG. 14A compares the secretion levels of IL-6, and FIG. 14B compares the secretion levels of TNF-α (SPC101, *Sphingomonas paucimobilis* EV; EV, extracellular vesicle).
Figure 14B:
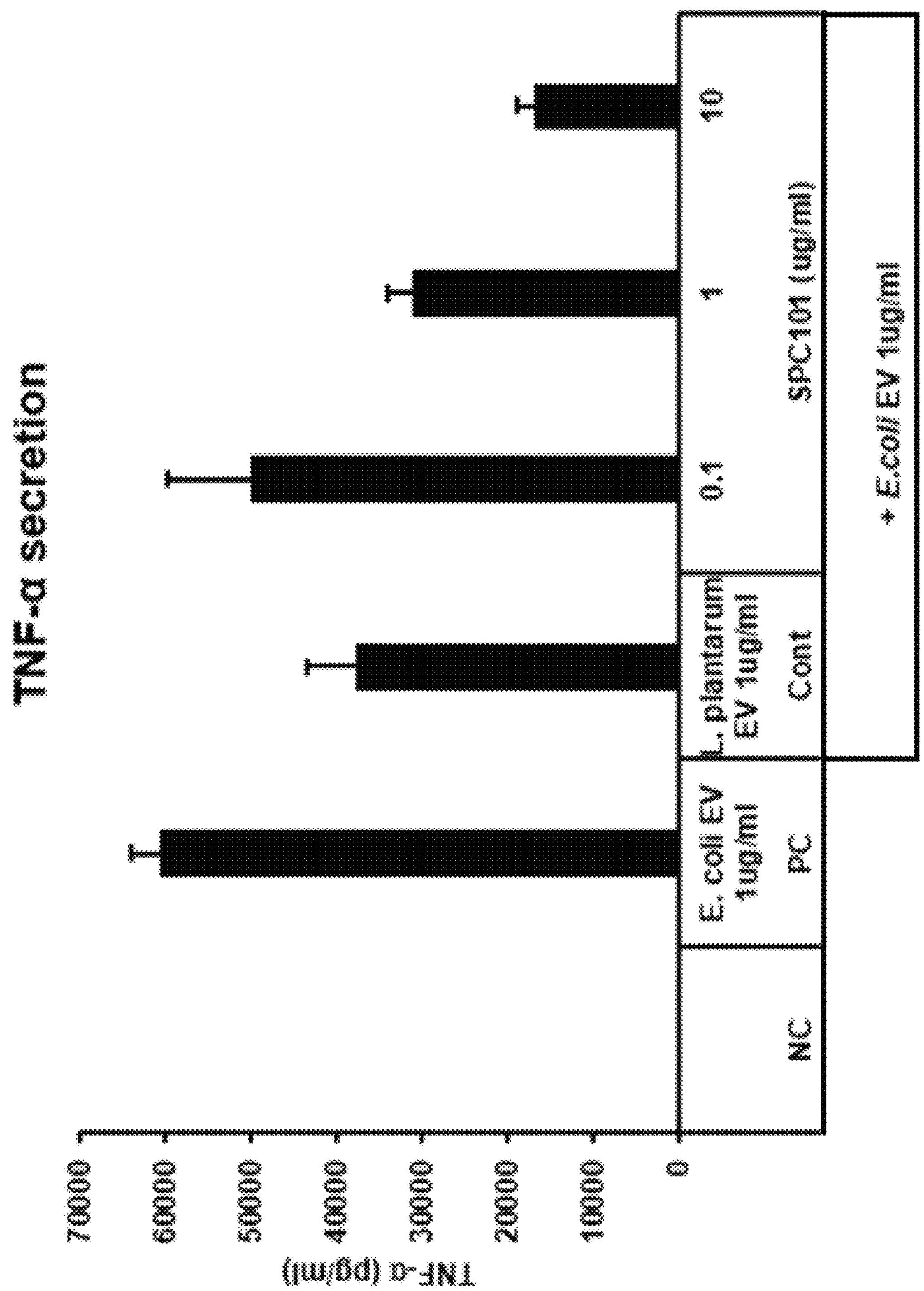

As a result, it was confirmed that upon pre-treatment with *Sphingomonas paucimobilis*-derived vesicles, the secretion of inflammatory mediators such as IL-6 (FIG. 14A) and TNF-α (FIG. 14B) induced in inflammatory cells by *E. coli*-derived vesicle stimulation was significantly suppressed (FIGS. 14A and 14B).

Example 16

Anti-Inflammatory Effects of *Sphingomonas Koreensis*-Derived Vesicles

In order to evaluate the anti-inflammatory effects of another bacteria belonging to the genus *Sphingomonas* based on the result of Example 14, after mouse macrophage cell lines were pre-treated with *Sphingomonas koreensis*-derived vesicles (SPC 102) at various concentrations (0.1, 1, and 10 μg/ml) for 12 hours, the cell lines were treated with 1 μg/ml of *E. coli*-derived vesicles, which are a pathogenic factor, and then the secretion of inflammatory cytokines was measured by ELISA after 12 hours.

Figure 15A:
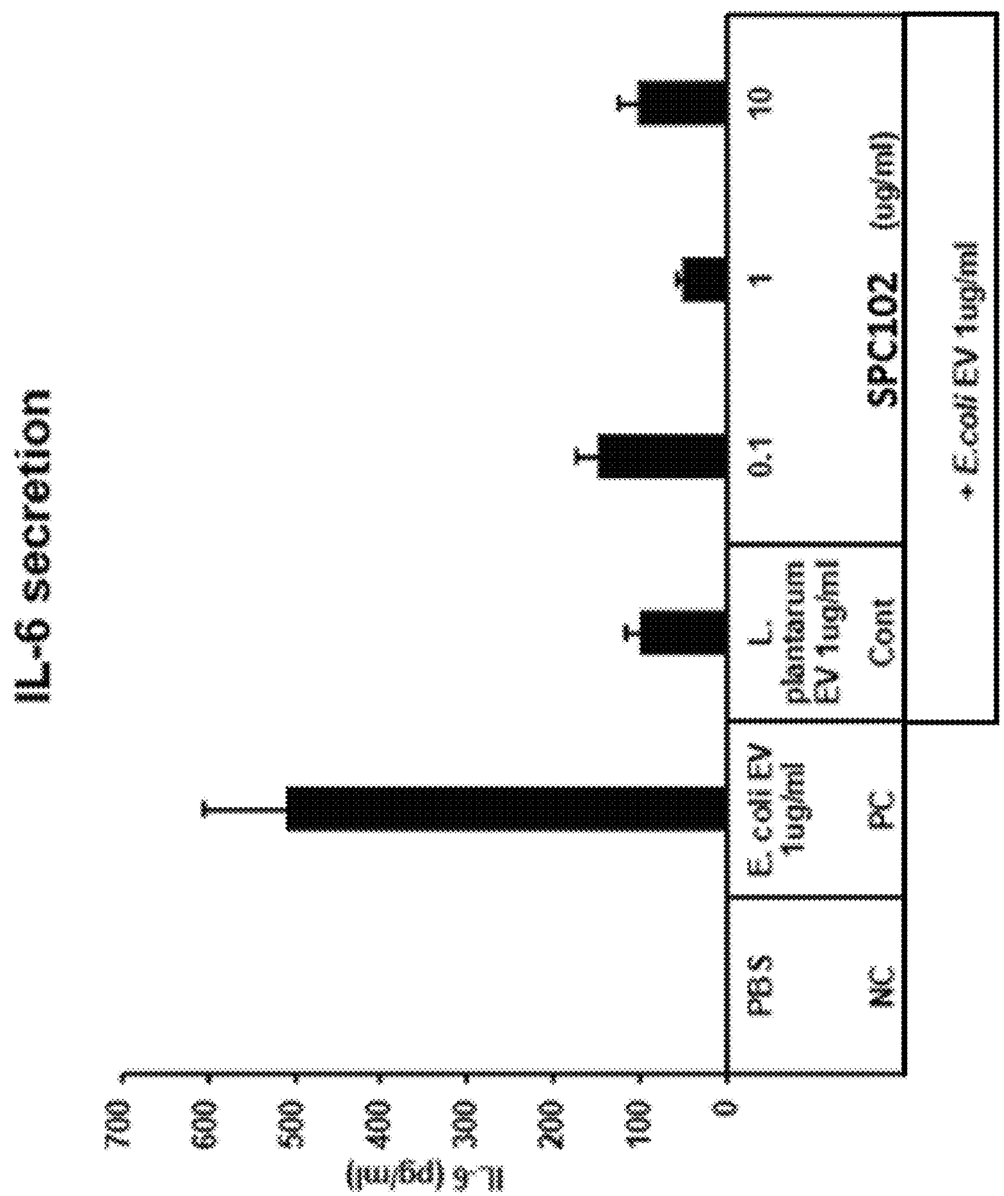
FIGS. 15A and 15B are results of evaluating effects of *E. coli* EV on the secretion of inflammatory mediators by pretreatment with *Sphingomonas koreensis*-derived vesicles prior to treatment with *E. coli* EV which is a pathogenic vesicle in order to evaluate the anti-inflammatory effects of *Sphingomonas koreensis*-derived vesicles, FIG. 15A compares the secretion levels of IL-6, and FIG. 15B compares the secretion levels of TNF-α (SPC102, *Sphingomonas koreensis* EV; EV, extracellular vesicle).
Figure 15B:
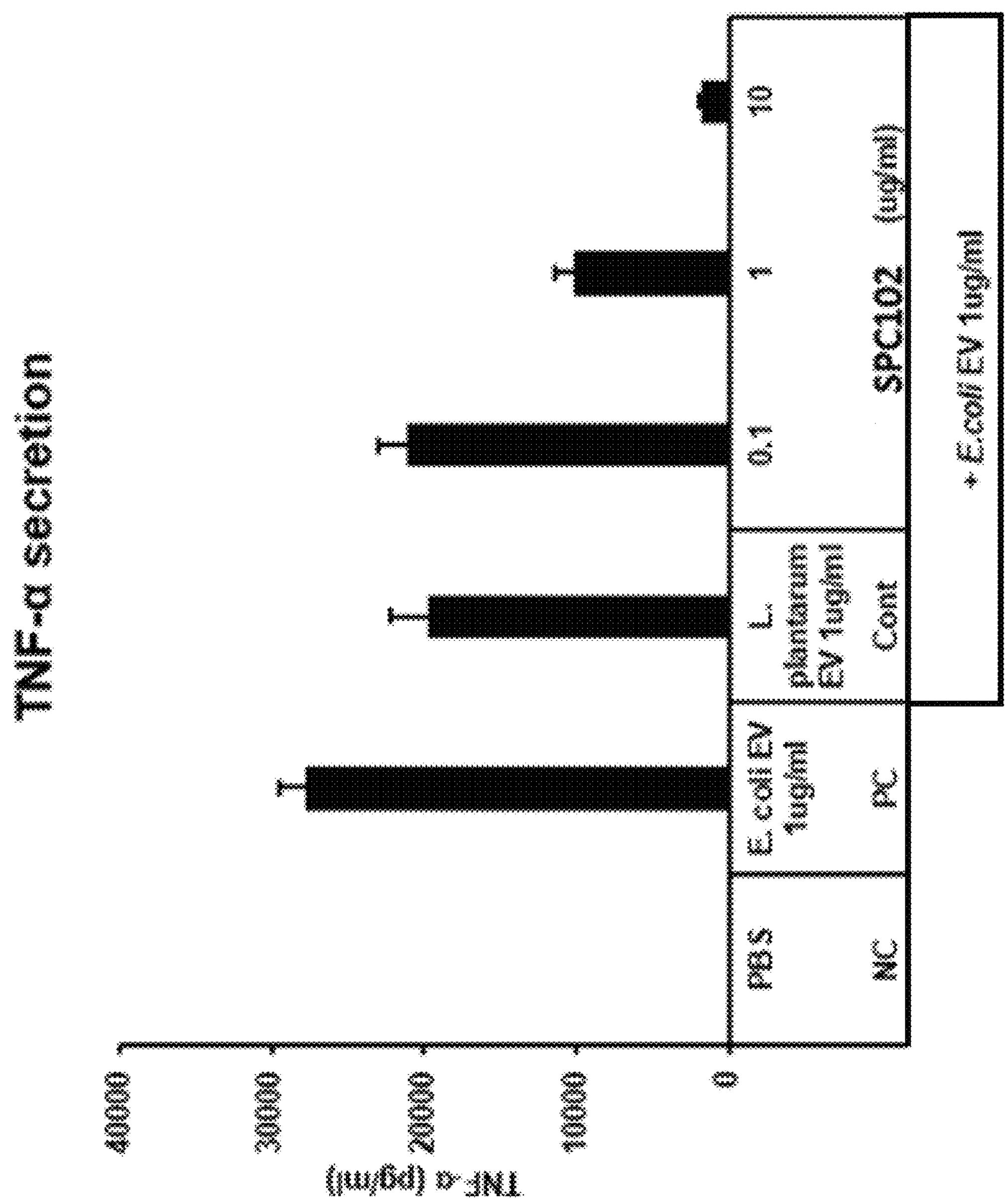

As a result, it was confirmed that upon pre-treatment with *Sphingomonas koreensis*-derived vesicles, the secretion of inflammatory mediators such as IL-6 (FIG. 15A) and TNF-α (FIG. 15B) induced in inflammatory cells by *E. coli*-derived vesicle stimulation was significantly suppressed (FIGS. 15A and 15B).

Example 17

Distribution Pattern of *Sphingomonas Paucimobilis*-Derived Vesicles

Figure 16:
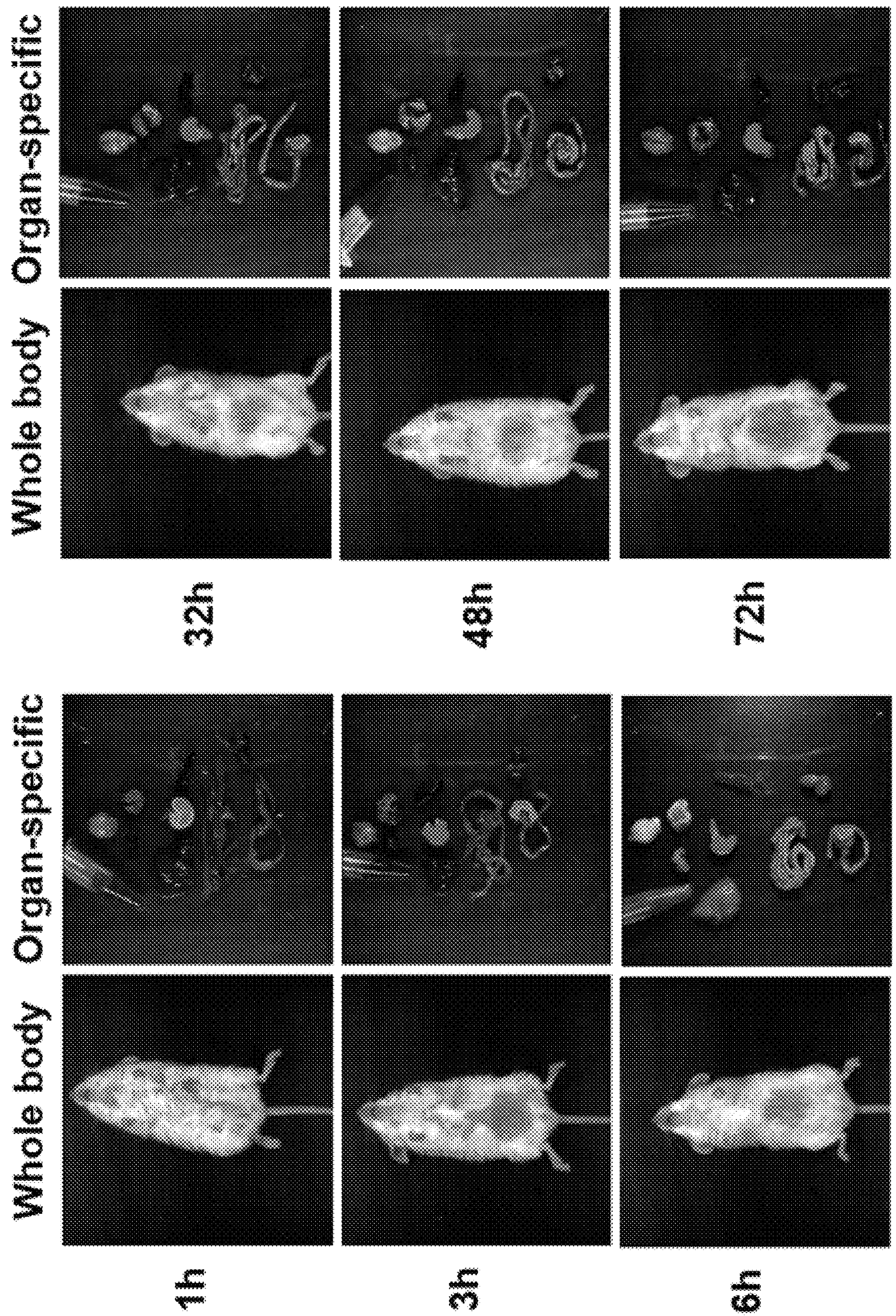
FIG. 16 is a series of photographs capturing distribution patterns of *Sphingomonas paucimobilis*-derived vesicles by time after the *Sphingomonas paucimobilis*-derived vesicles were orally administered to mice.

In order to confirm the absorption and distribution in organs by time when *Sphingomonas paucimobilis*-derived vesicles were orally administered, an experiment was performed as follows. 10 μg of fluorescence-labeled *Sphingomonas paucimobilis*-derived vesicles was orally administered, and fluorescence was measured after 1, 3, 6, 32, 48, and 72 hours, respectively. As a result of observing the fluorescence of the entire mouse image, it was confirmed that *Sphingomonas paucimobilis*-derived vesicles were distributed in the stomach from 1 hour after oral administration, and also distributed in the small intestine and the large intestine from 3 hours, and it was observed that the distribution in the organs was maintained until 72 hours (see FIG. 16).

Figure 17:
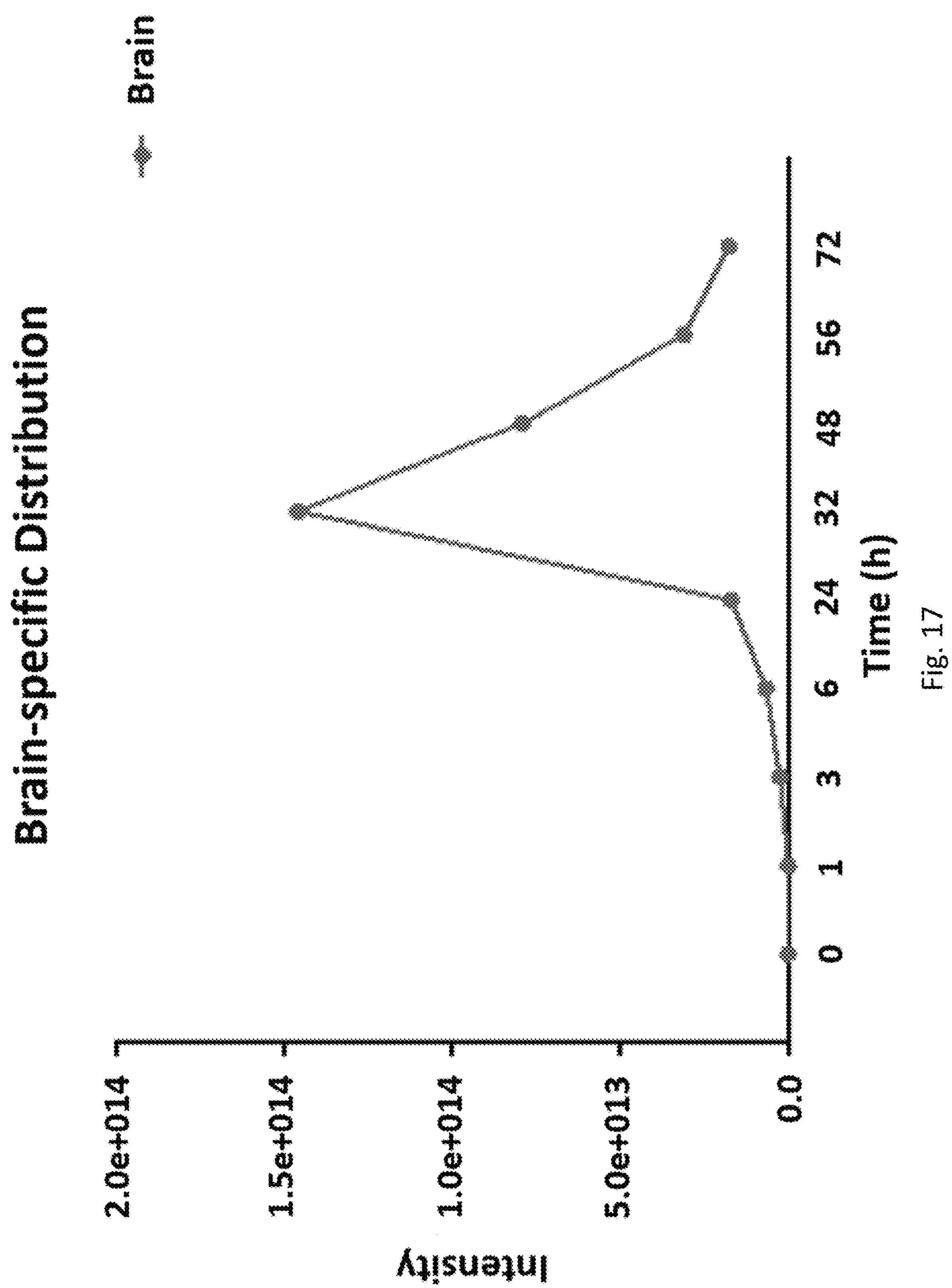
FIG. 17 is a series of views distribution patterns of *Sphingomonas paucimobilis*-derived vesicles in brain tissues by time after the *Sphingomonas paucimobilis*-derived vesicles were orally administered to mice.

In addition, it was confirmed that the fluorescence-labeled *Sphingomonas paucimobilis*-derived vesicles moved specifically to the brain from 3 hours, and it was confirmed that were the distribution degree of extracellular vesicles which had moved to the brain was increased until 32 hours, and then gradually decreased from 32 hours to 72 hours (see FIG. 17).

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

It was confirmed that vesicles derived from bacteria belonging to the genus *Sphingomonas* according to the present invention were absorbed in vivo through epithelial cells, systemically distributed, and excreted ex vivo through the kidneys, the liver, and the lungs, and it was confirmed that the vesicles were significantly reduced in blood or urine of a patient with hepatic cirrhosis, liver cancer, myocardial infarction, renal insufficiency, diabetes, a brain tumor, mild cognitive impairment, dementia, depression, autism, and atopic dermatitis, and the secretion of inflammatory mediators by pathogenic vesicles can be significantly suppressed. Therefore, the vesicles derived from bacteria belonging to the genus *Sphingomonas* according to the present invention are expected to have high industrial applicability value because the vesicles can be used as a method of diagnosing hepatic cirrhosis, liver cancer, myocardial infarction, renal insufficiency, diabetes, brain tumors, mild cognitive impairment, dementia, depression, autism, and atopic dermatitis, and as a composition for preventing, alleviating, or treating the diseases, such as a cosmetic, a food, or a drug, and furthermore can be usefully used as a drug carrier for delivering the drug to the brain.

The invention claimed is:

1. A method of alleviating or treating inflammation, the method comprising administering to a subject in need thereof a composition comprising an effective amount of vesicles derived from one or more selected from the group consisting of *Sphingomonas paucimobilis* and *Sphingomonas koreensis*.

2. The method of claim 1, wherein the vesicles have an average diameter of 10 to 200 nm.

3. The method of claim 1, wherein the vesicles are secreted naturally or artificially from one or more selected from the group consisting of *Sphingomonas paucimobilis* and *Sphingomonas koreensis*.

4. The method of claim 1, wherein the composition is a pharmaceutical composition, a food composition, or a cosmetic composition.

* * * * *